US010632469B2

(12) United States Patent
Hjelseth et al.

(10) Patent No.: US 10,632,469 B2
(45) Date of Patent: Apr. 28, 2020

(54) SAMPLE PROCESSING DEVICES, AND METHODS OF USE THEREOF

(71) Applicant: Douglas Scientific, LLC, Alexandria, MN (US)

(72) Inventors: Robert Hjelseth, Loretto, MN (US); Cory Hodgson, Alexandria, MN (US); Andrew Bristow, Alexandria, MN (US); Mark Baumgartner, Alexandria, MN (US); David Sellnow, Alexandria, MN (US); Cassie Keppel, Saint Louis, MO (US); John Steckelberg, Sauk Centre, MN (US); Paul Newman, Minnetonka, MN (US)

(73) Assignee: DOUGLAS SCIENTIFIC, LLC, Alexandria, MN (US)

( * ) Notice: Subject to any disclaimer, the term of this patent is extended or adjusted under 35 U.S.C. 154(b) by 0 days.

(21) Appl. No.: 16/219,737

(22) Filed: Dec. 13, 2018

(65) Prior Publication Data
US 2019/0184401 A1 Jun. 20, 2019

Related U.S. Application Data

(63) Continuation of application No. 15/579,887, filed as application No. PCT/US2016/036050 on Jun. 6, 2016.
(Continued)

(51) Int. Cl.
*B01L 3/00* (2006.01)
*C12M 1/00* (2006.01)
*C12N 15/10* (2006.01)

(52) U.S. Cl.
CPC ............... *B01L 3/5635* (2013.01); *B01L 3/50* (2013.01); *B01L 3/502* (2013.01); *B01L 3/508* (2013.01);
(Continued)

(58) Field of Classification Search
CPC ....... B01L 2200/026; B01L 2200/0631; B01L 2300/021; B01L 2300/042;
(Continued)

(56) References Cited

U.S. PATENT DOCUMENTS

| 5,128,104 A | 7/1992 | Murphy |
| 6,528,324 B1 | 3/2003 | Maiefski et al. |

(Continued)

FOREIGN PATENT DOCUMENTS

| DE | 3722562 | 1/1989 |
| GB | 2433219 | 6/2007 |

(Continued)

OTHER PUBLICATIONS

International Search Report issued in connection to International Patent Application No. PCT/US2016/036050; dated Dec. 21, 2016; 7 pages; Europe.

(Continued)

*Primary Examiner* — Jennifer Wecker
(74) *Attorney, Agent, or Firm* — Greenberg Traurig, LLP

(57) ABSTRACT

Embodiments of the invention provide a filter kit including filters for processing a biological sample. Some embodiments include a filter cap in a tube kit with a first tube containing a buffer solution and a second tube containing a lyophilized master mix. Some embodiments include a method of processing a sample using the kit including mixing a biological sample in a first tube with the buffer solution, positioning the filter cap in the first tube, positioning a second tube on the filter cap, flipping the first tube, the filter cap, and the second cap to filter the biological sample and buffer solution mixture with the filter cap as it flows from the first tube to the second tube. Some embodiments include structure enabling transfer of materials through inline flow between the tubes. Some further embodiments
(Continued)

include integrated structure for sample pulverization with integrated buffer and lyophilized master mix.

9 Claims, 22 Drawing Sheets

Related U.S. Application Data

(60) Provisional application No. 62/171,355, filed on Jun. 5, 2015.

(52) U.S. Cl.
CPC .............. *B01L 3/561* (2013.01); *C12M 45/06* (2013.01); *C12N 15/1017* (2013.01); *B01L 2200/026* (2013.01); *B01L 2200/0631* (2013.01); *B01L 2300/021* (2013.01); *B01L 2300/042* (2013.01); *B01L 2300/044* (2013.01); *B01L 2300/0681* (2013.01); *B01L 2300/0832* (2013.01); *B01L 2400/0457* (2013.01)

(58) Field of Classification Search
CPC ....... B01L 2300/044; B01L 2300/0681; B01L 2300/0832; B01L 2400/0457; B01L 3/50; B01L 3/502; B01L 3/508; B01L 3/561; B01L 3/5635; C12M 45/06; C12N 15/1017

See application file for complete search history.

(56) References Cited

U.S. PATENT DOCUMENTS

| | | |
|---|---|---|
| 2002/0197631 A1 | 12/2002 | Lawrence et al. |
| 2003/0134432 A1 | 7/2003 | Maiefski |
| 2004/0053319 A1 | 3/2004 | McWilliams |
| 2007/0014690 A1 | 1/2007 | Lawrence |
| 2008/0125704 A1 | 5/2008 | Anderson |
| 2011/0236960 A1 | 9/2011 | Bird et al. |
| 2013/0266948 A1 | 10/2013 | Bird |
| 2015/0258548 A1 | 9/2015 | Bird et al. |
| 2016/0069781 A1 | 3/2016 | Middlebrook et al. |

FOREIGN PATENT DOCUMENTS

| | | |
|---|---|---|
| WO | 2005/106460 | 11/2015 |
| WO | 2016/036464 | 3/2016 |
| WO | 2016/197123 | 12/2016 |

OTHER PUBLICATIONS

European Patent Office; PCT Written Opinion of the International Searching Authority issued in connection to International Patent Application No. PCT/US2016/036050; dated Dec. 21, 2016; 13 pages; Europe.

SAMPLE PROCESSING DEVICES, AND METHODS OF USE THEREOF

RELATED APPLICATIONS

This application is a continuation application of U.S. application Ser. No. 15/579,887, filed Dec. 5, 2017, which is a 371 National Stage application of PCT/US2016/036050, filed Jun. 6, 2016, which claims the benefit of and priority to U.S. Provisional Application No. 62/171,355, filed on Jun. 5, 2015, the entire contents of which are incorporated herein by reference.

BACKGROUND

The processing of raw biological samples for extraction of DNA for genetic profiling usually requires multiple vessels that are used through a plurality of processing steps. Typically, separate vessels are used for one or more different biochemical analysis steps, including taking the sample, disrupting the sample with chemical or mechanical means, extracting DNA from the sample, and analyzing the sample. Not only is the use of multiple vessels time-consuming and costly, the introduction of multiple surfaces and transfer of samples from one vessel to another can increase the risk of contamination that can introduce errors during the downstream sample analysis step. Accordingly, there is a need to integrate and miniaturize various sample processing steps into a unitary or modular device, to significantly reduce or eliminate the need to transfer biological samples between multiple separate vessels. A modular design can increase the efficiency of extracting nucleic acids from tissue samples, and increase efficiency by largely eliminating the need to transfer reactants between separate reaction vessels to perform each step of the extraction process. Furthermore, integration of the device with external automation equipment modular designs can allow the extraction process to be performed with only one action from the user, thereby enabling the process to be fully automated after the user initiates the extraction process.

SUMMARY

Some embodiments include a filter kit comprising a center portion, and a first connection portion coupled to a first side of the center portion, where the first connection portion is coupled to a first tube containing a buffer solution. Further, a second connection portion is coupled to a second side of the center portion, where the second connection portion is coupled to a second tube containing a lyophilized master mix. Further, the filter cap includes a first filter at least partially located in the first connection portion, and a second filter at least partially located in the second connection portion. In some further embodiments, the filter cap comprises a third filter at least partially located in the center portion of the filter cap.

Some embodiments include a tube kit comprising a first tube containing a buffer solution, and a second tube containing a lyophilized master mix. The kit also includes a filter cap comprising a center portion, a first connection portion coupled to a first side of the center portion, and a second connection portion coupled to a second side of the center portion. Further, the kit also includes a first filter at least partially located in the first connection portion, and a second filter at least partially located in the second connection portion.

In some embodiments, the first connection portion of the filter cap is configured to be positioned in a cavity in the first tube to form at least a partial mechanical seal with the first tube. In some further embodiments, the second connection portion of the filter cap is configured to be positioned in a cavity in the second tube to form at least a partial mechanical seal with the second tube.

Some embodiments include a first adhesive on the first side of the center portion of the filter cap around the first connection portion, where the first adhesive is configured to form a seal between the filter cap and the first tube. Further, a second adhesive on the second side of the center portion of the filter cap around the second connection portion is configured to form a seal between the filter cap and the second tube.

Some embodiments include a method comprising placing a biological sample in a first tube that is preloaded with a buffer solution, where a biological sample and buffer solution mixture is formed. Further, the method includes positioning a filter cap in the first tube, positioning a second tube on the filter cap, flipping the first tube, the filter cap, and the second cap, and filtering the biological sample and buffer solution mixture with the filter cap as it flows from the first tube to the second tube. Some further embodiments include positioning the filter cap in the first tube that includes positioning a first connection portion of the filter cap in the first tube. Some other embodiments include positioning a second tube on the filter cap that includes positioning a second tube on a second connection portion of the filter cap.

Some embodiments of the invention include a tube kit comprising a first tube containing a buffer solution, where there is an opening at a first end of the first tube and a seal across a second end of the first tube. Further, the tube kit comprises a second tube containing a lyophilized master mix, and a lid with a tip coupled to the lid, where the second end of the first tube is configured to form a seal with the first end of the second tube, and where the tip coupled to the lid is configured to puncture the seal on the second end of the first tube as the lid is placed on the first tube.

In some embodiments, the first tube sits in the second tube. In some further embodiments, the first tube clips onto the second tube. In other embodiments, the lid has a bulb top. In some further embodiments, the second tube includes a filter.

Some embodiments include a method comprising adding a biological sample to a first tube containing a buffer solution, where the biological sample is added through an opening at a first end of the first tube, and positioning a second end of the first tube in a second tube, puncturing a seal on the second end of the first tube with a tip coupled to a lid, and positioning the lid on the first tube to form a seal between the lid and the first tube.

Some embodiments include an inline sample processing device comprising a first chamber configured to receive a tissue sample and a nucleic acid extraction reagent, where the first chamber is configured to permit the tissue sample to be pulverized. Further, the method includes a second chamber in flow communication with the first chamber that is configured to receive the extraction reagent and a portion of the pulverized tissue sample. Further, the device includes a first separation element disposed between the first chamber and the second chamber and configured to permit a portion of the pulverized tissue sample and the extraction reagent to flow from the first chamber to the second chamber. Further, a third chamber is in flow communication with the second chamber, and has a plurality of ports configured to allow a reagent to be delivered to the third chamber, and a second separation element is disposed between the second chamber and the third chamber and is configured to substantially prevent the pulverized tissue from entering the third chamber.

Some embodiments include a sample processing device for pulverization and denaturation comprising a hollow cylindrical portion, a hollow tapered portion, a first cap for covering an end of the cylindrical portion, and a second cap for covering an end of the tapered portion. Further, the device can include a plurality of ribs extending along the cylindrical portion, a ring at an end of the plurality of ribs where the cylindrical portion meets the tapered portion, and a pulverizer contained within the cylindrical portion between the ring and the first cap.

In some embodiments, the pulverizer is cylindrical or spherical. In some further embodiments, the pulverizer is glass, ceramic, stainless steel, or a non-reactive polymer. In some other embodiments, the plurality of ribs prevents the pulverizer from touching sides of the sample processing device and allows the pulverizer to slide within the cylindrical portion. In some further embodiments, the ring prevents the pulverizer from entering the tapered portion of the sample processing device.

Some embodiments include a method for pulverizing and denaturing a crude sample comprising placing a pulverizer in a sample processing device. The device can comprise a cylindrical portion, a tapered portion, and a plurality of ribs extending along the cylindrical portion, and a ring at an end of the plurality of ribs where the cylindrical portion meets the tapered portion. The method can include placing the crude sample in the cylindrical portion of the sample processing device, sealing the sample processing device, and shaking the sample processing device such that the pulverizer macerates the crude sample to create a pulverized sample. Further, the method can include adding a denaturing agent into the tapered portion of the sample processing device, sealing the sample processing device, and shaking the sample processing device such that the denaturing agent denatures DNA within the pulverized sample to create a denatured sample. Some embodiments comprise transferring the denatured sample into a testing vessel. Other embodiments include testing the denatured sample in the sample processing device.

Some embodiments of the invention include the sample processing device comprising a tube comprising a removable basket with a grid and a plurality of tabs that hang over an edge of the tube, a barcode, and a cap comprising a ring-shaped punch edge for punching a sample out of a crude biological material, and a plurality of fingers or teeth for forcing the sample through the grid of the removable basket in the tube.

In some embodiments of the invention, the cap snaps onto the tube. In other embodiments, the cap twists onto the tube. Some further embodiments include a sample processing liquid. In other embodiments, the sample processing liquid is a lysis buffer in the tube. In some further embodiments, the sample processing liquid is sodium hydroxide contained within a pouch in the tube or the cap. In other embodiments, the tube further comprises a permeable layer adjacent to the sodium hydroxide pouch. In some embodiments, the cap further comprises a piercer. In some further embodiments, the cap further comprises a septum.

DETAILED DESCRIPTION

Figure 1A:
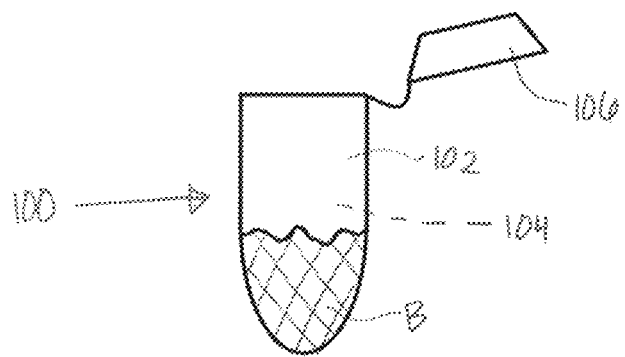
FIG. 1A is side view of a first tube in accordance with some embodiments of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Unless specified or limited otherwise, the terms "tube" or "tubes, and variations thereof are used broadly and encompass any cross-sectional shape and/or any shape of container.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives that fall within the scope of embodiments of the invention.

Figure 1B:
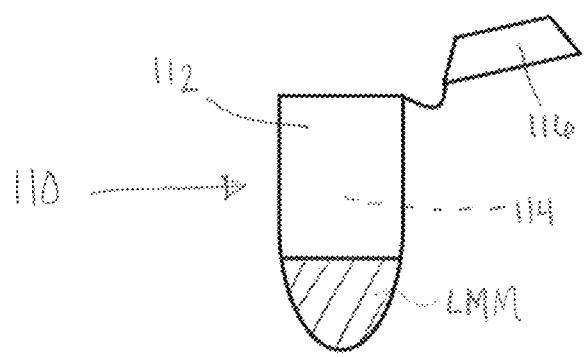
FIG. 1B is a side view of a second tube in accordance with some embodiments of the invention.

FIG. 1A is side view of first tube 100 in accordance with some embodiments of the invention. In some embodiments, the first tube 100 includes body 102 at least partially enclosing or forming the cavity 104, and a lid 106. As illustrated in FIG. 1A, in some embodiments, the lid 106 can be coupled or tethered to the body 102. In some other embodiments, the lid 106 can be detached from or independent from the body 102, and later coupled to the body 102 when required. For example, in some embodiments, the lid 106 can be sized to be positioned in the cavity 104 to at least partially seal the first tube 100. In some embodiments, the lid 106 can be coupled to the body 102 using any conventional coupling. FIG. 1B is a side view of second tube 110 in accordance with some embodiments of the invention. In some embodiments, the second tube 110 shown in FIG. 1B can include a body 112, cavity 114, and a lid 116. In some embodiments, the lid 116 can be coupled to the body 112. In some other embodiments, the lid 116 can be detached from the body 112, and later coupled to the body 112 when required. For example, in some embodiments, the lid 116 can be sized to be positioned in the cavity 114 to at least partially seal the first tube 110. In some embodiments, the lid 116 can be coupled to the body 112 using any conventional coupling. In some further embodiments of the invention, body 102 and/or body 112 can be used without a lid (i.e., lid 106 and/or lid 116 can be absent). In some embodiments, the first tube 100 and/or the second tube 110 and include a generally rounded or curved end. In other embodiments, the first tube 100 and/or the second tube 110 can comprise a closed end that comprises a flat or square end.

Referring again to FIG. 1A, in some embodiments, the first tube 100 can contain a volume of buffer solution B in cavity 104 of the body 102. In some embodiments, the volume of buffer solution B can at least partially fill the first tube 100 (shown in this non-limiting embodiment as filling the closed end of the first tube 100 including the rounded or curved portion). In other embodiments, more or less volume of buffer solution B can be added or included in the first tube 100 (e.g., in a kit). Referring again to FIG. 1B, in some embodiments, the second tube 110 can contain a lyophilized master mix LMM in cavity 114 of the body 112. In some embodiments, the volume of lyophilized master mix LMM can at least partially fill the second tube 110 (shown in this non-limiting embodiment as at least partially filling the closed end of the second tube 110 including the rounded or curved portion). In other embodiments, more or less volume of lyophilized master mix LMM can be added or included in the second tube 110.

Figure 1C:
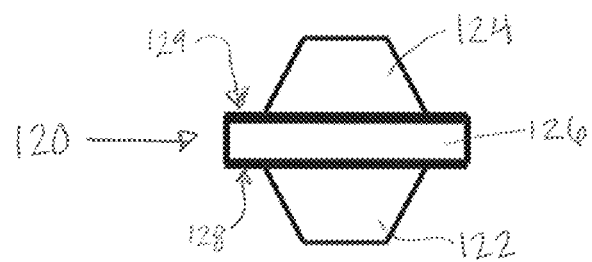
FIG. 1C is a side view of a filter cap in accordance with some embodiments of the invention.

FIG. 1C is a side view of filter cap 120 in accordance with some embodiments of the invention. In some embodiments, the filter cap 120 can include a first connection portion 122, a second connection portion 124, and a center portion 126 positioned substantially between the first connection portion 122 and the second connection portion 124. In some embodiments, the filter cap 120 can be coupled with the first tube 100 and/or the second tube 110 and used to perform one or more filtering functions of material within the tubes 100, 110. In some embodiments, the first connection portion 122 can be coupled to a first side of center portion 126 and second connection portion 124 is coupled to a second side of center portion 126. Further, in some embodiments, the first connection portion 122, and/or the second connection portion 124, and/or the center portion 126 can include one or more filters. In some embodiments, the first connection portion 122 of filter cap 120 can be sized to be positioned in cavity 104 of the first tube 100 to form at least a partial seal between the filter cap 120 and the first tube 100. Further, in some embodiments, the second connection portion 124 of filter cap 120 can be sized to be positioned in cavity 114 of the second tube 110 to form at least a partial seal between filter cap 120 and second tube 110. In some embodiments of the invention, the filter cap 120 can include a first adhesive 128 on the first side of center portion 126 around first connection portion 122, and a second adhesive 129 on the second side of center portion 126 around the second connection portion 124. In some embodiments, the first adhesive 128 and second adhesive 129 can hold the filter cap 120 in position in the first tube 100 and the second tube 110 when the filter cap 120 is positioned in the first tube 100 and second tube 110. Further, in some embodiments, the positioning of the filter cap 120 with adhesives 128, 129 can prevent leakage between the filter cap 120 and the first tube 100 and second tube 110. In an alternate embodiment of the invention, the first adhesive 128 and/or second adhesive 129 can be omitted, and the filter cap 120 can at least partially seal against first tube 100 and second tube 110 using a conventional mechanical seal.

Figure 2:
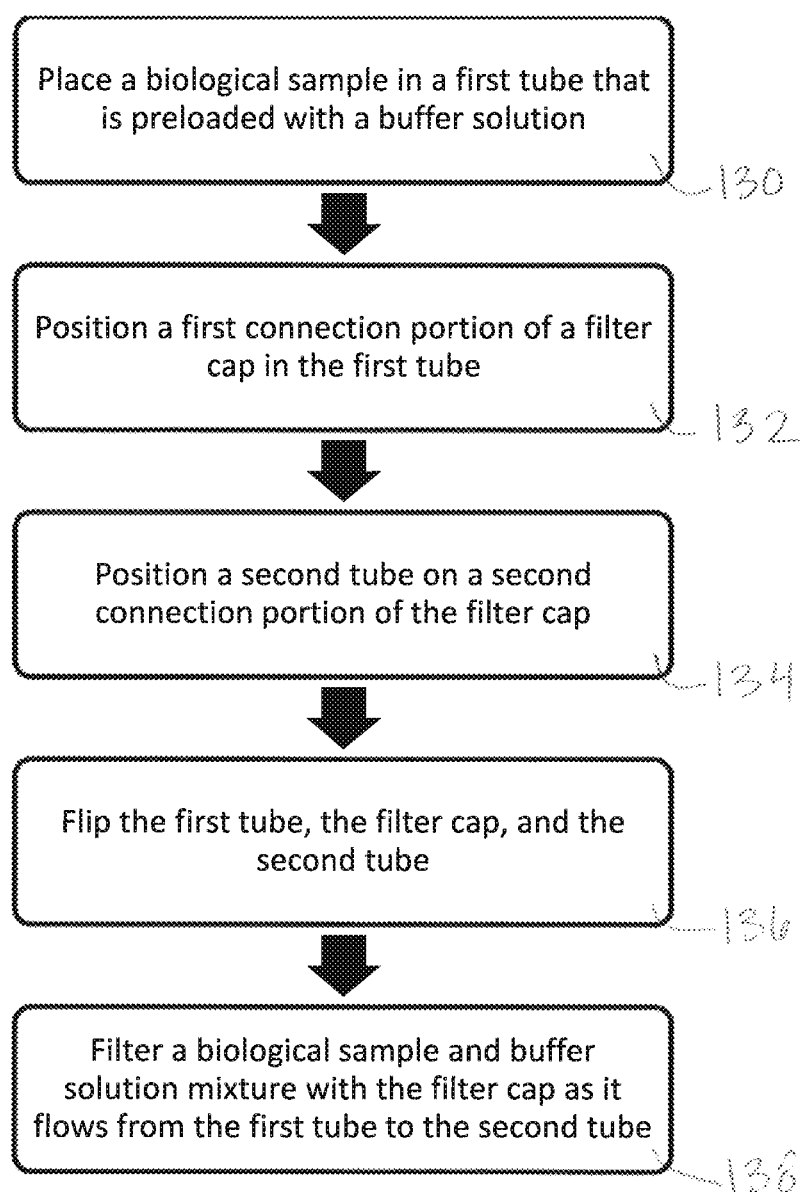
FIG. 2 is a flow chart showing the steps of preparing a biological sample for testing in accordance with some embodiments of the invention.

FIG. 2 is a flow chart showing the steps of preparing biological sample S for testing in accordance with some embodiments of the invention. In some embodiments, FIG. 2 includes steps 130, 132, 134, 136, and 138. In some embodiments, the steps of preparing biological sample S for testing can include the order as shown. In other embodiments, any of the steps 130, 132, 134, 136, 138 can proceed in a different order than shown. Further, in some embodiments, any of the steps 130, 132, 134, 136, 138 can be included, omitted, or repeated.

Figure 3:
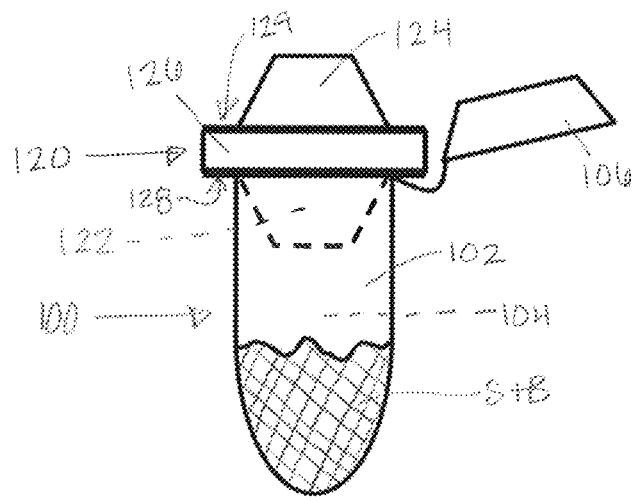
FIG. 3 is a side view of the filter cap positioned on the first tube in accordance with some embodiments of the invention.
Figure 4:
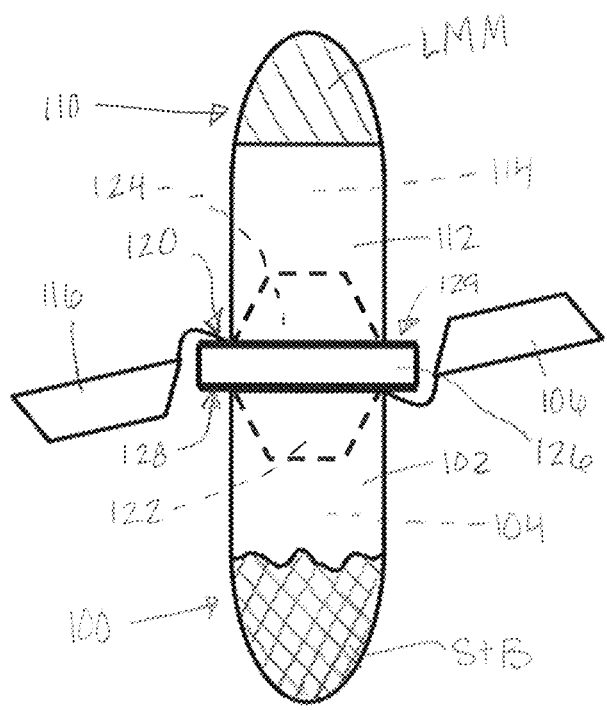
FIG. 4 is a side view of the filter cap positioned between the first tube and the second tube in accordance with some embodiments of the invention.
Figure 5:
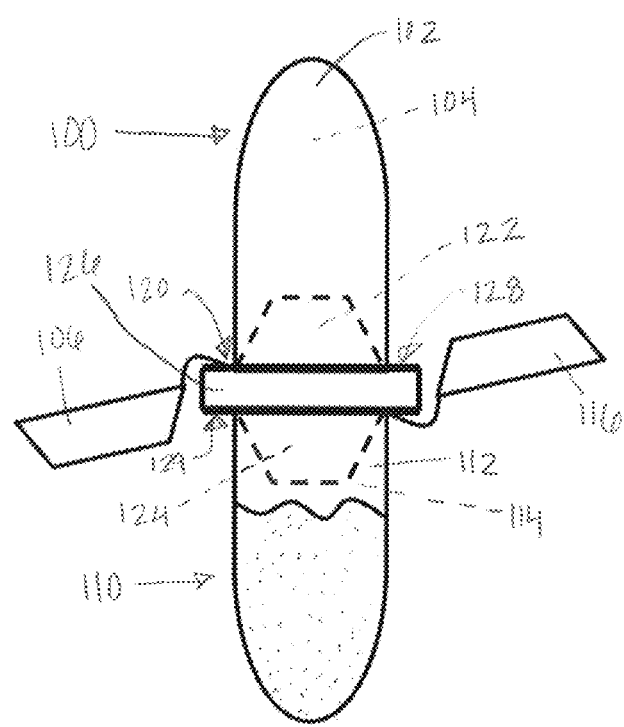
FIG. 5 is a side view of the filter cap positioned between the first tube and the second tube in accordance with some embodiments of the invention.

In some embodiments of the invention, the filter cap 120 can be positioned between the first tube 100 and the second tube 110 to enable filtering a biological sample. For example, FIGS. 3-5 show steps 132, 134, and 138, respectively. FIG. 3 is a side view of filter cap 120 positioned on first tube 100 in accordance with some embodiments of the invention. FIG. 4 is a side view of filter cap 120 positioned between first tube 100 and second tube 110 in accordance with some embodiments of the invention. In some embodiments of the invention, step 130 can include placing biological sample S in a first tube 100 that contains buffer solution B. In some embodiments, first tube 100 can have buffer solution B placed or pre-loaded in first tube 100 prior to the collection of a biological sample S. In some embodiments, the buffer solution B in the first tube 100 can vary depending on what biological sample S is to be tested. In some embodiments of the invention, the biological sample S can be pipetted into the first tube 100 to mix with buffer solution B in the first tube 100. In some embodiments, this can create a biological sample S and buffer solution B mixture (S+B). In some embodiments, the biological sample and buffer solution mixture S+B can be heated in the first tube 100 if needed.

In some embodiments of the invention, with the lid 106 positioned away from the open end of the body 102, step 132 can include positioning a first connection portion 122 of filter cap 120 in first tube 100, as seen in FIG. 3. In some embodiments, the first connection portion 122 of filter cap 120 can form at least a partial seal with first tube 100. In some embodiments, first adhesive 128 can be applied to the first side of center portion 126 of filter cap 120 around the first connection portion 122 to strengthen the seal between filter cap 120 and first tube 100. Further, in some embodiments, the first adhesive 128 can help to prevent biological sample and buffer solution mixture S+B from leaking out of first tube 100.

In some embodiments, step 134 can include positioning the second tube 110 on the second connection portion 124 of filter cap 120, as seen in FIG. 4. In some embodiments, the second tube 110 can have lyophilized master mix LMM placed or pre-loaded in the second tube 110 prior to the collection of biological sample S. In some embodiments, lyophilized master mix LMM preloaded in second tube 110 can vary depending on what biological sample S is to be tested. In some embodiments, the second connection portion 124 of filter cap 120 can form at least a partial seal with the second tube 110. In some embodiments, the second adhesive 129 can be applied to the second side of center portion 126 of filter cap 120 around second connection portion 124 to strengthen the seal between filter cap 120 and second tube 110.

In some embodiments, step 138 can include filtering the biological sample and buffer solution mixture S+B through filter cap 120. In some embodiments of the invention, step 136 can include rotating, turning and/or flipping the first tube 100, filter cap 120, and second tube 110. In some embodiments, the rotating, turning and/or flipping the first tube 100, filter cap 120, and second tube 110 can include a single rotation, turn or flip. In other embodiments, the rotating, turning and/or flipping the first tube 100, filter cap 120, and second tube 110 can include multiple or repeated rotating, turning and/or flipping. In some embodiments, the action of rotating, turning and/or flipping can agitate the contents of the first tube 100 and/or the second tube 110.

In some embodiments, this movement can allow the biological sample and buffer solution mixture S+B to flow through the filter cap 120 into the second tube 110. In some embodiments, the second adhesive 129 that is positioned between filter cap 120 and second tube 110 can help prevent biological sample and buffer solution mixture S+B from leaking out of filter cap 120 and second tube 100 as the biological sample and buffer solution mixture S+B flows through the filter cap 120 into the second tube 110. For example, FIG. 5 is a side view of filter cap 120 positioned between first tube 100 and second tube 110 in accordance with some embodiments of the invention. In this non-limiting example, the positions of the first tube 100 and second tube 110 are flipped about 180° than that illustrated in FIG. 4, and the biological sample and buffer solution mixture S+B has exited the first tube 100 and entered the second tube 110 through filter cap 120. In some embodiments, the filter cap 120 can include filters to filter contamination or other unwanted or undesirable material in the biological sample and buffer solution mixture S+B. In some embodiments, the biological sample and buffer solution mixture S+B can be filtered through filter cap 120, and can mix with the lyophilized master mix LMM in the second tube 110. In some embodiments, this can create a final mixture FM (which includes biological sample S, buffer solution B, and lyophilized master mix LMM) for testing. In some embodiments of the invention, the filter cap 120 can be removed from second tube 110 and lid 116 of second tube 110 can be positioned in the cavity 114 of the second tube 110 to at least partially seal the final mixture FM in the second tube 110. In some embodiments, the second tube 110 can then be positioned in a device for testing.

In some embodiments, the filter cap 120 can allow fluid to flow in both directions. In a further embodiment, the filter cap 120 can act as a check valve, and can allow fluid to flow single direction (e.g., from the first tube 100 to the second tube 110 but not from the second tube 110 to the first tube 100). In the method described above for instance, filter cap 120 can allow biological sample and buffer solution mixture S+B to flow from the first tube 100 to a second tube 110, but not from the second tube 110 to the first tube 100.

In some embodiments. the first tube 100, second tube 110, and filter cap 120 can allow a user to prepare a crude biological sample S for testing in the field. In some embodiments of the invention, the first tube 100, second tube 110, and filter cap 120 are advantageous, as they can allow a user to prepare biological sample S for testing in the field using minimal instruments. For example, in some embodiments, the first tube 100 and the second tube 110 can be conventional or standard tubes that are preloaded with a buffer solution B and lyophilized master mix LMM necessary for performing a particular task. In some embodiments, the crude biological sample S can then be placed in the first tube 100 in the field, and mixed with buffer solution B. In some embodiments, the filter cap 120 can be positioned on the first tube 100 and second tube 110 can be placed on the filter cap 120. In some embodiments, the first tube 100, second tube 110, and filter cap 120 can then be flipped and agitated so that at least some portion of the biological sample and buffer solution mixture S+B can flows from the first tube 110 to second tube 120. In some embodiments, the rotating, turning and/or flipping the first tube 100, filter cap 120, and second tube 110 can include at least one rotation, turn or flip. In some embodiments, the action of rotating, turning and/or flipping can agitate the contents of the first tube 100 and/or the second tube 110.

In some embodiments of the invention, the filter cap 120 can filter contamination or other unwanted or undesirable material out of biological sample and buffer solution mixture S+B. In some embodiments, the biological sample and buffer solution mixture S+B that flows into second tube 120 can then be mixed with lyophilized master mix LMM in second tube 120. In some embodiments, this further processes biological sample S to prepare biological sample S for testing. Further, in some embodiments, the second tube 110 can be removed from the filter cap 120 and lid 116 of second tube 110 can closed. In some embodiments, the second tube 110 can then be placed in a device for testing.

Figure 6A:
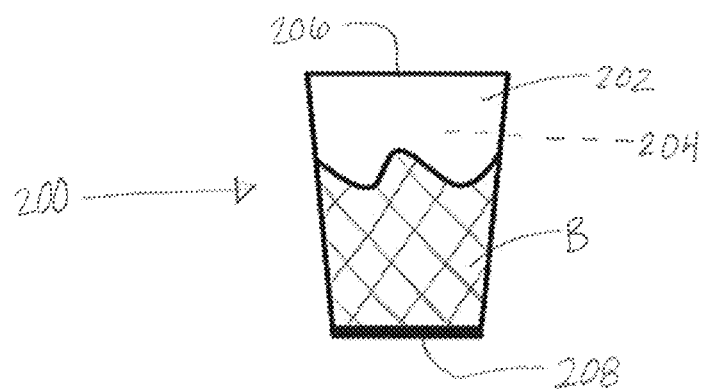
FIG. 6A is side view of a first tube in accordance with some further embodiments of the invention.
Figure 6B:
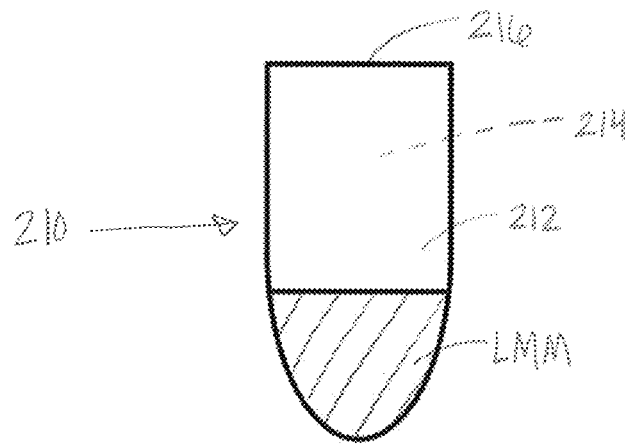
FIG. 6B is a side view of a second tube in accordance with some further embodiments of the invention.

FIG. 6A is side view of first tube 200 in accordance with some further embodiments of the invention. In some embodiments, the first tube 200 can include a body 202 at least partially enclosing a cavity 204. Further, the first tube 200 can include an opening 206 at one end, and seal 208 at an opposite end. In some embodiments, the first tube 200 can comprise a generally square or flat end proximate the seal 208. FIG. 6B is a side view of second tube 210 in accordance with some further embodiments of the invention. In some embodiments, the second tube 210 can include a body 212, cavity 214 formed in the body 212, and an opening 216 positioned at a first end of the cavity 214. In the non-limiting example embodiments shown, the second tube 210 can include a closed end comprising a generally rounded or curved end. In some embodiments, the first tube 200 can contain a buffer solution B in the cavity 204 of body 202. Further, in some embodiments, the second tube 210 can contain a lyophilized master mix LMM positioned in the cavity 214 of body 212.

Figure 6C:
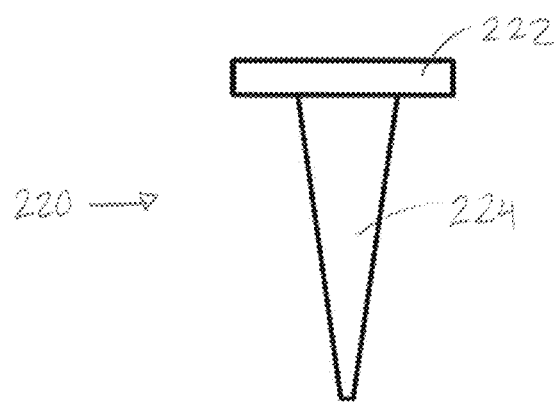
FIG. 6C is a side view of a lid in accordance with some further embodiments of the invention.

FIG. 6C is a side view of lid 220 in accordance with some further embodiments of the invention. In some embodiments, the lid 220 can include a lid portion 222 and pipette tip 224. In some embodiments, the pipette tip 224 is coupled to and extends from a first side of lid portion 222 of the lid 220. In some embodiments of the invention, the lid 220 can be positioned in a tube (e.g., such as tubes 200, 210) so that pipette tip 224 can extend into the tube, and the lid portion 222 forms at least a partial seal with at least a portion of the tube.

Figure 7:
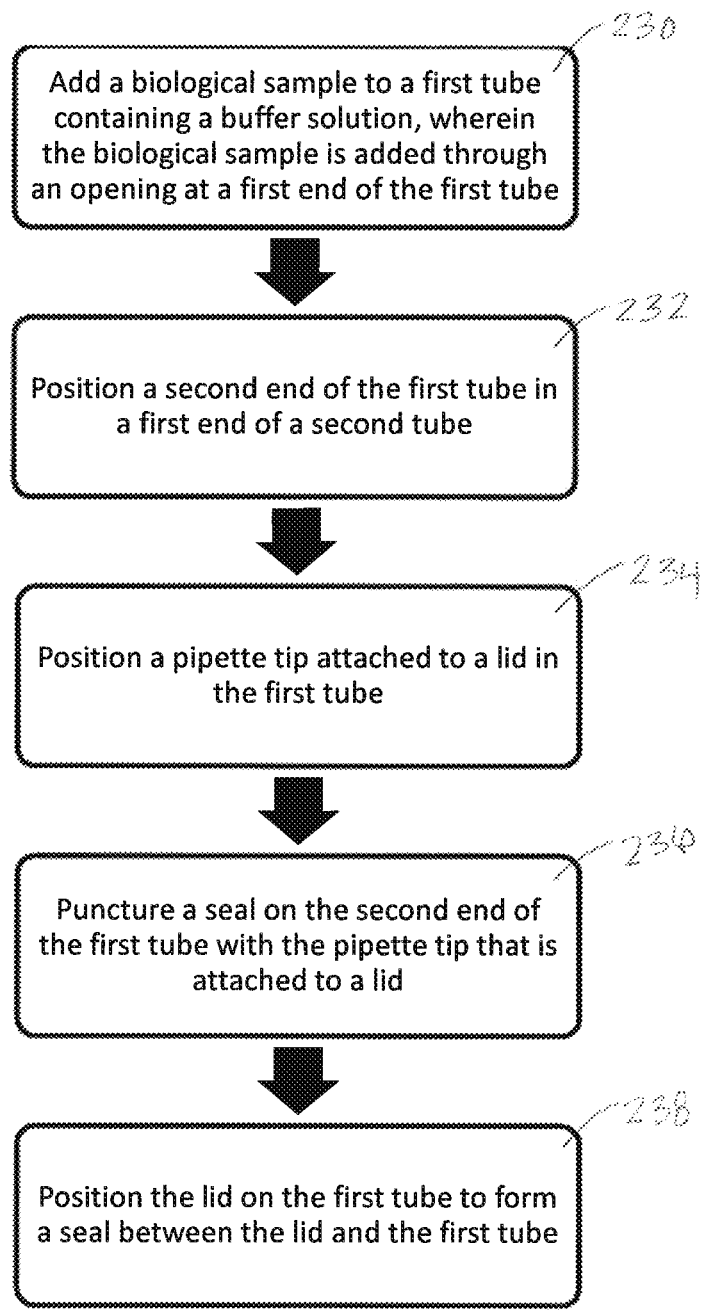
FIG. 7 is a flow chart showing the steps of preparing a biological sample for testing in accordance with some embodiments of the invention.

In some embodiments of the invention, the first tube 200 and/or the second tube 210 and/or the pipette tip 224 can be configured to process a sample (e.g., such as a biological sample). For example, FIG. 7 is a flow chart showing the steps of preparing biological sample S for testing in accordance with some embodiments of the invention. FIG. 7 includes steps 230, 232, 234, 236, and 238. In some embodiments, the steps of preparing biological sample S for testing can include the order as shown. In other embodiments of the invention, any of the steps 230, 232, 234, 236, 238 can proceed in a different order than shown. Further, in some embodiments, any of the steps 230, 232, 234, 236, 238 can be included, omitted, or repeated.

Figure 8:
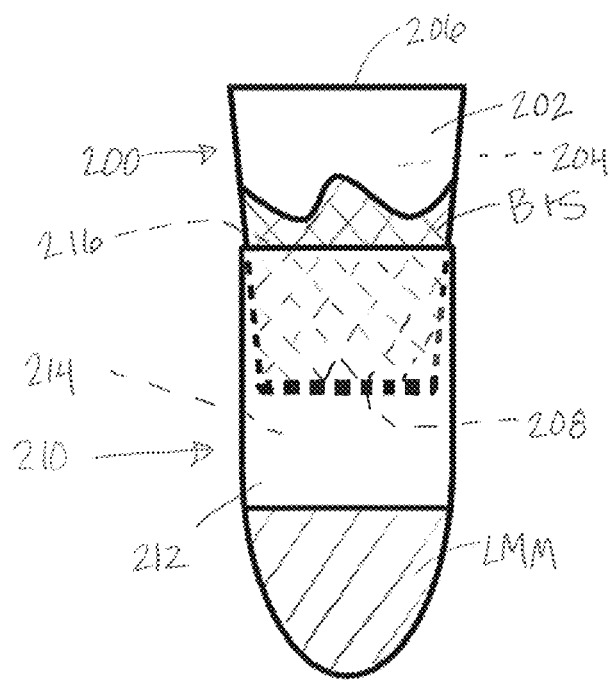
FIG. 8 is a side view of the first embodiment of the first tube positioned in the first embodiment of the second tube in accordance with some embodiments of the invention.
Figure 9:
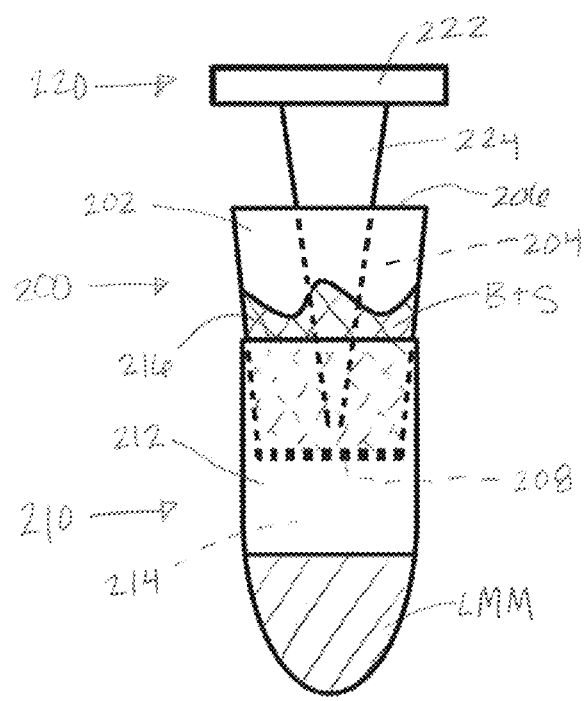
FIG. 9 is a side view of the first embodiment of the first tube positioned in the first embodiment of the second tube with the first embodiment of the lid being placed in the first tube in accordance with some embodiments of the invention.
Figure 10:
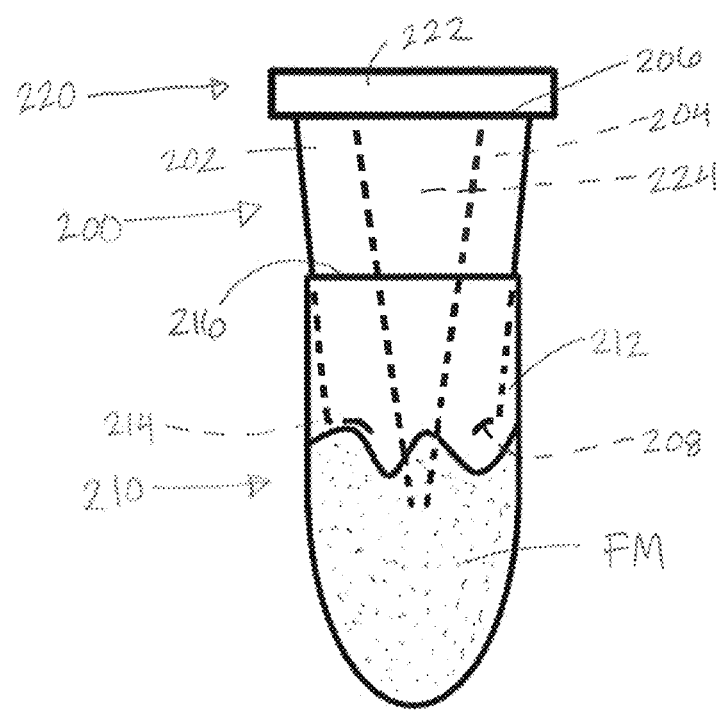
FIG. 10 is a side view of the first embodiment of the first tube positioned in the first embodiment of the second tube with the first embodiment of the lid fully placed on the first tube in accordance with some embodiments of the invention.

FIGS. 8-10 illustrate views representing at least one or more of the process steps of FIG. 7. FIG. 8 is a side view of the first tube 200 positioned in the second tube 210 in accordance with some embodiments of the invention, and FIG. 9 is a side view of the first tube 200 positioned in the second tube 210 with lid 220 being placed in the first tube 200 in accordance with some embodiments of the invention. Further, FIG. 10 is a side view of the first tube 200 positioned in second tube 210 with lid 220 fully placed on the first tube 200 in accordance with some embodiments of the invention.

Referring to FIG. 7, step 230 can include adding biological sample S to a first tube 200 that contains buffer solution B. As illustrated in FIG. 6A, buffer solution B can be placed in the first tube 200 prior to the collection of biological sample S. In some embodiments, the buffer solution B in first tube 200 can vary depending on the type of biological sample S. In some embodiments, the biological sample S can be pipetted into opening 206 of first tube 200 to mix with the buffer solution B in the cavity 204 to create a biological sample S and buffer solution B mixture (B+S).

In some embodiments, step 232 includes positioning a second end of the first tube 200 in the second tube 210, as seen in FIG. 8. The second end of first tube 200 has smaller diameter than the diameter of the first end of second tube 210, thereby allowing the insertion of at least a portion of the first tube 200 into the cavity 214. In some embodiments, the body 202 of first tube 200 include walls that slope based on a smaller diameter of the body 202 at the second end to a larger diameter of the body 202 at the first end. Thus, in some embodiments, when the second end of first tube 200 is positioned in the second tube 210 as described earlier, the first tube 200 can at least partially slide into the second tube 210 until the an outer diameter of first tube 200 is about the diameter of the inner diameter of the first end of the second tube 210. In some embodiments, this can form at least a partial seal between the first tube 200 and the second tube 210. In some embodiments of the invention, the second tube 210 contains lyophilized master mix LMM. In some embodiments, the lyophilized master mix LMM in second tube 110 can vary depending on what biological sample S is to be tested.

In some embodiments of the invention, step 234 can include positioning the pipette tip 224 of lid 220 in the first tube 200, as seen in FIG. 9. In some further embodiments of the invention, step 236 can include puncturing the seal 208 on the first tube 200 with the pipette tip 224 of lid 220. In some embodiments, the pipette tip 224 of lid 220 can be longer than the first tube 200, and thus in some embodiments, as the pipette tip 224 of lid 220 is positioned in first tube 200, the pipette tip 224 can contact the seal 208 of the first tube 200. In some embodiments of the invention, the pipette tip 224 can puncture the seal 208 of the first tube 200 as pipette tip 224 is moved through the first tube 200 and into the second cavity 214. In an alternative embodiment, pipette tip 224 can be a sharp tip capable of puncturing seal 208 but without pipetting capabilities. In some embodiments, the puncturing seal 208 can cause biological sample and buffer solution B+S to flow from first tube 200 into second tube 210. In some embodiments, the biological sample and buffer solution B+S can then mix with lyophilized master mix LMM to form a final mixture FM that is suitable for testing.

In some embodiments, step 238 can include positioning the lid portion 222 of lid 220 on the first tube 200 to form at least a partial seal between the lid 220 and the first tube 200, as seen in FIG. 10. Further, as the pipette tip 224 is moved as described above, after the pipette tip 224 punctures the seal 208, it can extend through the first tube 200 and into the second tube 210 until the lid portion 222 of lid 220 comes into contact with first tube 200. In some embodiments, this can form a seal between the lid 220 and the first tube 200. Further, in some embodiments, the lid 220, first tube 200, and second tube 210 can then be placed in a device for testing.

In some embodiments of the invention, the first tube 200, second tube 210, and lid 220 can allow a user to prepare a crude biological sample S for testing in the field. In some embodiments, the lid 220, first tube 200, and second tube 210 are advantageous, as they allow a user to prepare biological sample S for testing in the field using minimal instruments. For example, in some embodiments, the first tube 200 and the second tube 210 can have a buffer solution B and lyophilized master mix LMM added to them, and can then be taken into the field. In some embodiments, a crude biological sample S can then be collected in the field and placed in the first tube 200, and mixed with buffer solution B. In some embodiments of the invention, the first tube 200 can then be positioned in second tube 210 to form at least a partial seal between first tube 200 and second tube 210. In some embodiments, the pipette tip 224 of lid 220 can then be positioned in first tube 200 and moved through first tube 200. In some embodiments, as the pipette tip 224 moves through first tube 200, it can contact with and puncture the seal 208 on first tube 200 as described earlier. In some embodiments, this can cause the field-sampled biological sample and buffer solution mixture B+S to flow into the second tube 210, where the biological sample and buffer solution mixture B+S can mix with the lyophilized master mix LMM. In some embodiments, the steps as described can further process the biological sample S for testing by placing the Lid 220, first tube 200, and second tube 210 in a testing device.

Figure 11A:
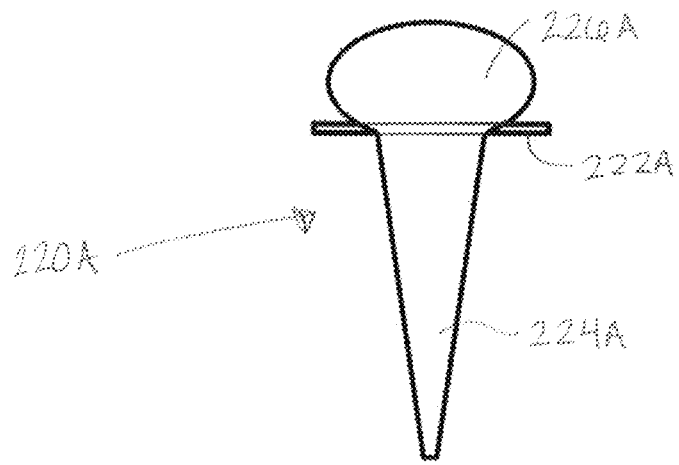
FIG. 11A is a side view of a second embodiment of a lid.
Figure 11B:
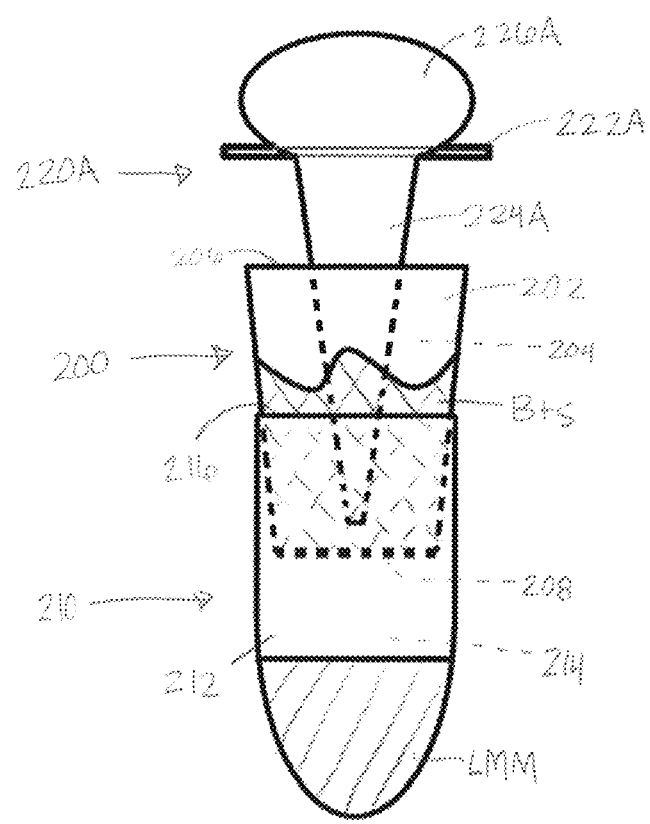
FIG. 11B is a side view of the first embodiment of the first tube positioned in the first embodiment of the second tube with the second embodiment of the lid being placed in the first tube in accordance with some embodiments of the invention.

In some embodiments, the first tube 200 and the second tube 210 can be used with alternative types of lid structures. For example, FIG. 11A is a side view of the lid 220A in accordance with some embodiments of the invention, and FIG. 11B is a side view of the first tube 200 positioned in the second tube 210 with lid 220A being placed in the first tube 200 in accordance with some embodiments of the invention. In some embodiments, the lid 220A can include a lid portion 222A, pipette tip 224A, and bulb portion 226A. In some embodiments, the pipette tip 224A can be coupled to the first side of the lid portion 222A, and the bulb portion 226A can be coupled to a second side of the lid portion 222A. In some embodiments, the bulb portion 226A can include a cavity that is coupled to a cavity of pipette tip 224A. In some embodiments, this structure can enable the lid 220A to act as a pipette. For example, in some embodiments, a user can grasp and squeeze the bulb portion 226A, place the pipette tip 224A in a fluid, and release the bulb portion 226A to suck the fluid into the pipette tip 224A. In some embodiments, the use of the lid 220A with the first tube 200 and the second tube 210 can allow a user to use the lid 220A to pipette the biological sample S into the first tube 200 to mix with buffer solution B. In some embodiments, the pipette tip 224A of lid 220A can then be used to puncture the seal 208 in the first tube 200 and lid portion 222A of lid 220A can seal against first tube 200, as described in reference to FIGS. 6A-10 above.

Figure 12A:
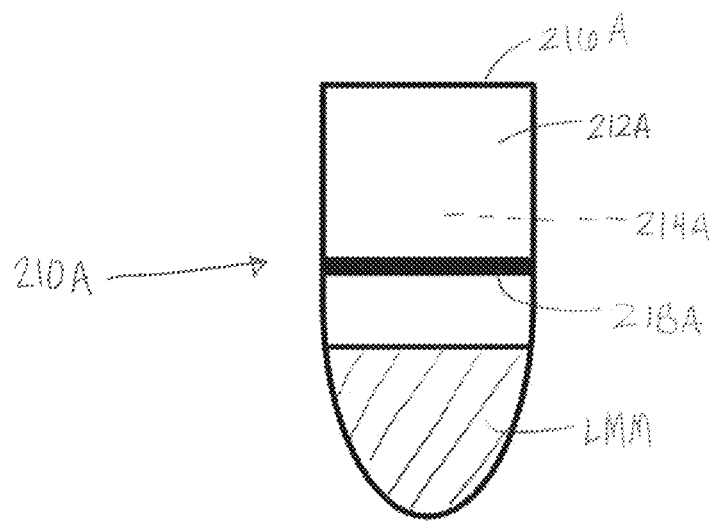
FIG. 12A is a side view of a second embodiment of the second tube.
Figure 12B:
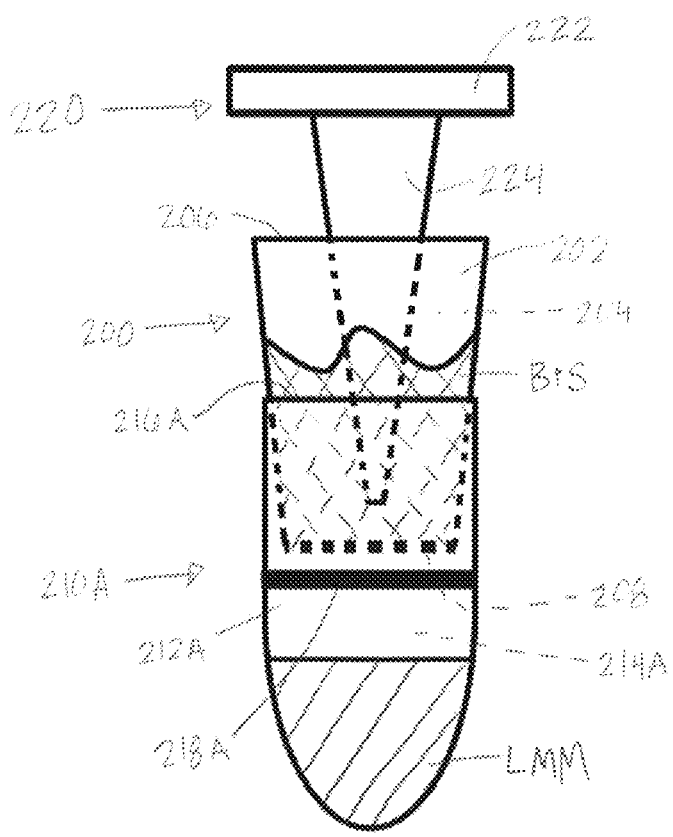
FIG. 12B is a side view of the first embodiment of the first tube positioned in the second embodiment of the second tube with the first embodiment of the lid being placed in the first tube in accordance with some embodiments of the invention.

In some embodiments, the second tube 210 can include an integrated filter. For example, FIG. 12A is a side view of a second tube 210A in accordance with some embodiments of the invention. FIG. 12B is a side view of the first tube 200 positioned in the second tube 210A with the lid 220 being placed in the first tube 200 in accordance with some embodiments of the invention. In some embodiments, the second tube 210A can include body 212A, cavity 214A formed by the body 212A, opening 216A, and filter 218A positioned in the cavity 214A extending from one side of the body 212A to an opposite side of the body 212A. In some embodiments of the invention, the opening 216A can be positioned at a first end of the cavity 214A in the second tube 210A. In some embodiments of the invention, the second tube 210A can contain lyophilized master mix LMM in the cavity 214A of the body 212A of the second tube 210A. In some embodiments, the steps and processes described above in FIGS. 6A-10 can be performed with the first tube 200 in combination with a second tube including an integrated filter. For example, as seen in FIG. 12B, the first tube 200 can be positioned above the filter 218A in the second tube 210A. In some embodiments, once the seal 208 of the first tube 200 is punctured, a biological sample and reagent mixture B+S can flow from the first tube 200 through the filter 218A into the second tube 210A. In some embodiments, the filter 218A can filter contamination or other unwanted or undesirable material in the biological sample and buffer solution mixture S+B. In some embodiments, filtering contamination or other unwanted or undesirable material from the biological sample and reagent mixture B+S can improve the accuracy of testing of biological sample and reagent mixture B+S.

Figure 13A:
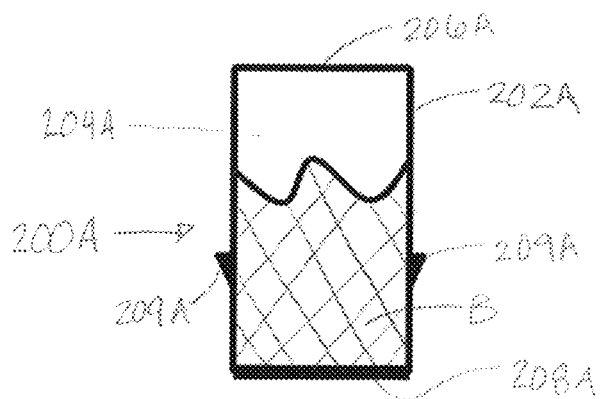
FIG. 13A is a cross-sectional view of a first tube in accordance with some further embodiments of the invention.
Figure 13B:
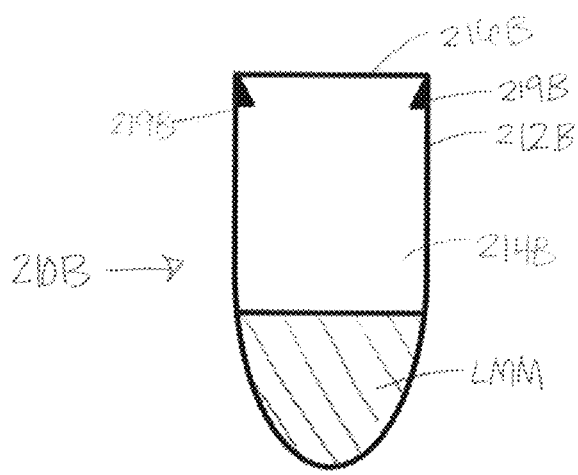
FIG. 13B is a cross-sectional view of a second tube in accordance with some other embodiments of the invention.
Figure 13C:
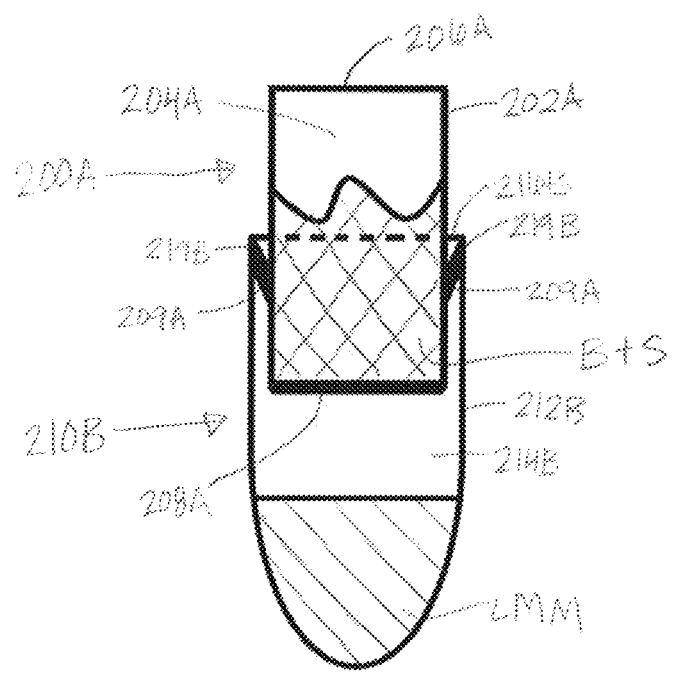
FIG. 13C is a cross-sectional view of the second embodiment of the first tube positioned in the third embodiment of the second tube in accordance with some embodiments of the invention.
Figure 13D:
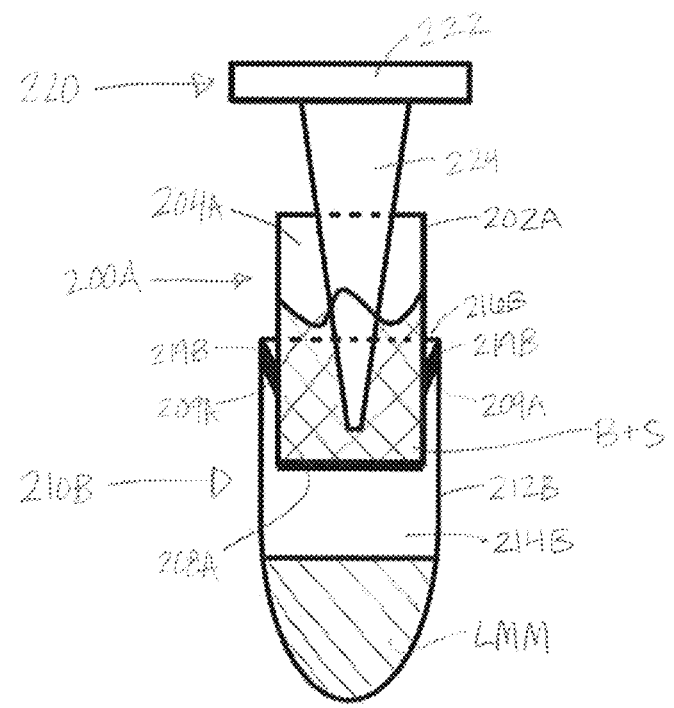
FIG. 13D is a cross-sectional view of the second embodiment of the first tube positioned in the third embodiment of the second tube with the first embodiment of the lid being placed in the first tube in accordance with some embodiments of the invention.

FIG. 13A is a cross-sectional view of a first tube 200A in accordance with some further embodiments of the invention. In some embodiments, the first tube 200A can include body 202A at least partially enclosing the cavity 204A, an opening 206A at one end of the cavity 204A, and a seal 208A at an opposite end of the cavity 204A, and flange 209A. In some embodiments, the first tube 200A further contains flange 209A positioned around an outside diameter of body 202A. In some embodiments, the flange 209A can be positioned between the first end and the second end of first tube 200A. In some embodiments, the flange 209A can include a flat face on a first side and an angled face on a second side. FIG. 13B is a cross-sectional view of a second tube 210B in accordance with some other embodiments of the invention. In some further embodiments, the second tube 210B can include body 212B, cavity 214B, opening 216B, and flange 219B. In some embodiments, the first tube 200A and second tube 210B can be used to process a sample using a lid such as the lid 220. For example, FIG. 13C is a cross-sectional view of the first tube 200A positioned at least partially in the second tube 210B in accordance with some embodiments of the invention, and FIG. 13D is a cross-sectional view of first tube 200A positioned in second tube 210B with the lid 220 being placed in first tube 200A in accordance with some embodiments of the invention. In some embodiments, the first tube 200A can contain buffer solution B in cavity 204A of body 202A of first tube 200A, and when the first tube 200A is positioned in the second tube 210B, as seen in FIGS. 13C-13D, the flanges 209A can engage the flanges 219B to prevent first tube 200A from being pulled out of second tube 210B. In some embodiments, as the first tube 200A is positioned in the second tube 210B, the angled faces of flanges 209A can slide against the angled faces of flange 219B.

In some embodiments, as the first tube 200A moves into the second tube 210B, the faces of flanges 209A can slide at least partially past or over the angled faces of flange 219B. In some embodiments, the flanges 209A can couple with the inner surface of the second tube 210B, and/or at least a portion of the flange 219B. In other embodiments, any conventional coupling mechanism can be used to couple the first tube 200A to the second tube 210B, and can be used to substantially retain the first tube 200A in the second tube 210B as shown in FIGS. 13C-13D.

In some embodiments, once the first tube 200A fully positioned in the second tube 210B, the flat face of the flange 209A can sit against the flat face of flange 219B. In some embodiments, this engagement can prevent the first tube 200A from being removed from the second tube 210B, and can also prevent contamination from passing into second tube 210B. In reference to FIG. 13C, in some embodiments, after the first tube 200A is positioned in the second tube 210B, the pipette tip 224 of the lid 220 can then be pushed through first tube 200A to puncture seal 208A on first tube 200A, and the lid 220 can at least partially seal against the first tube 200A. In other embodiments, the various embodiments of first tube 200, second tube 210, and lid 220 described in FIGS. 6-13D above can be integrated with one another in any way.

Figure 14:
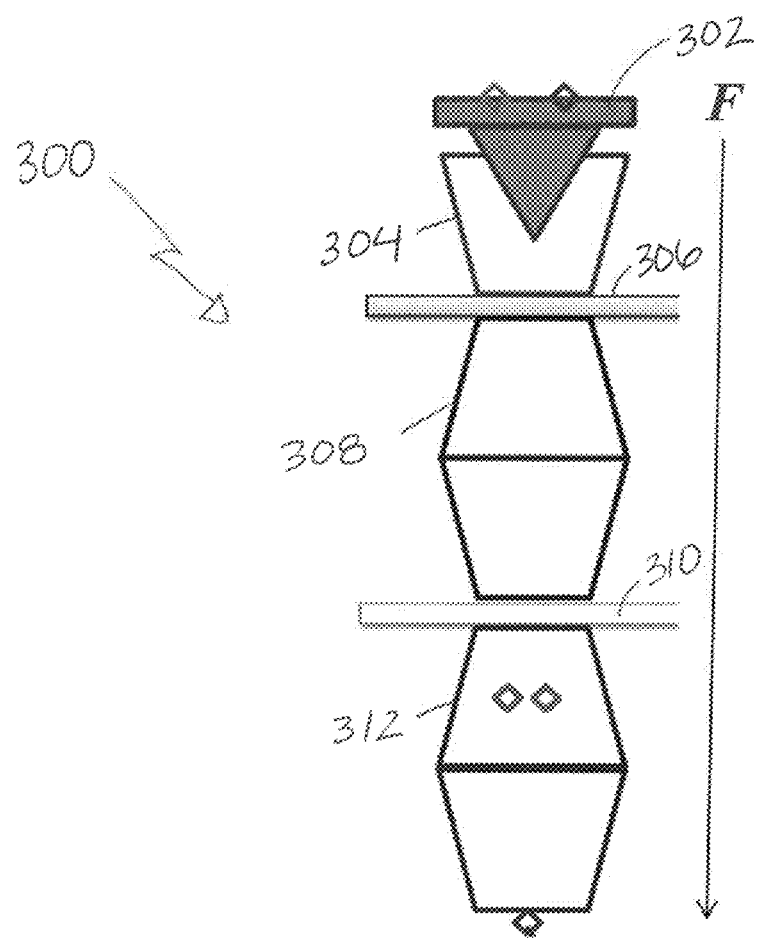
FIG. 14 is a plan view of a multi-chamber inline sample processing device in accordance with some embodiments of the invention.

FIG. 14 is a plan view of multi-chamber inline sample processing device 300 in accordance with some embodiments of the invention. In some embodiments, the sample processing device 300 can include three inline chambers, which together define an inline flow path of a material through the sample processing device 300. In some embodiments of the invention, the sample processing device 300 can include cap 302, pulverization chamber 304, first separation element 306, extraction chamber 308, second separation element 310, and dilution chamber 312. In some embodiments, the size and volume of each chamber of device 300 can be scaled to match the quantity of material to be processed. In this way, each of chambers, 304, 308, and 312 can be sized according to the quantity of material to be processed. For example, in some embodiments, chamber 304 can be sized smaller to process single seeds or leaf punches or sized larger to accommodate a collection of seeds or other material that form a representative sample of a large collection of material to be analyzed. Furthermore, each of the chambers 304, 308, 312, cap 302, and separation elements 306, 310 of device 300 can be sized independently based on the application and quantity of materials needed.

In some embodiments of the invention, the sample processing device 300 can be formed as a single piece. In some embodiments, the sample processing device 300 can be formed using a mold and first separation element 306 and second separation element 310 can be press fit into the sample processing device 300. In other embodiments, each of the chambers 304, 308, and 312 can be separate modules that when coupled together form the sample processing device 300. Additionally, in some embodiments, each of the chambers 304, 308, and 312 can have other shapes other than the frustoconical shapes depicted in FIG. 14. As an example, each chamber 304, 308, or 312 can have a cylindrical shape.

In some embodiments, the cap 302 can be coupled to the pulverization chamber 304 at an upstream end of pulverization chamber 304 with respect to a direction F of flow. Terms such as upstream and downstream as used in this description refer to relative positions along the direction of flow F. In some embodiments, the first separation element 306 can be coupled both to a downstream end of pulverization chamber 304 and to an upstream end of the extraction chamber 308. In some embodiments, the second separation element 310 can be coupled both to a downstream end of extraction chamber 308 and to an upstream end of dilution chamber 312. In operation, a biological sample, such as a plant tissue, seed, or a combination of material from different sources can be pulverized or mechanically distressed in pulverization chamber 304. In some embodiments, a portion of the pulverized tissue can be passed through the first separation element 306 and into the extraction chamber 308. In some embodiments of the invention, nucleic acids can be extracted from the plant tissue within the extraction chamber 308. In some embodiments, the extracted nucleic acids can then pass through the second separation element 310 and into the dilution chamber 312. In some embodiments, in the dilution chamber 312, the extracted nucleic acids can be neutralized with a neutralization buffer and diluted with water or a dilution buffer. The specific structure and operation of each chamber is described in further detail below.

Figure 15A:
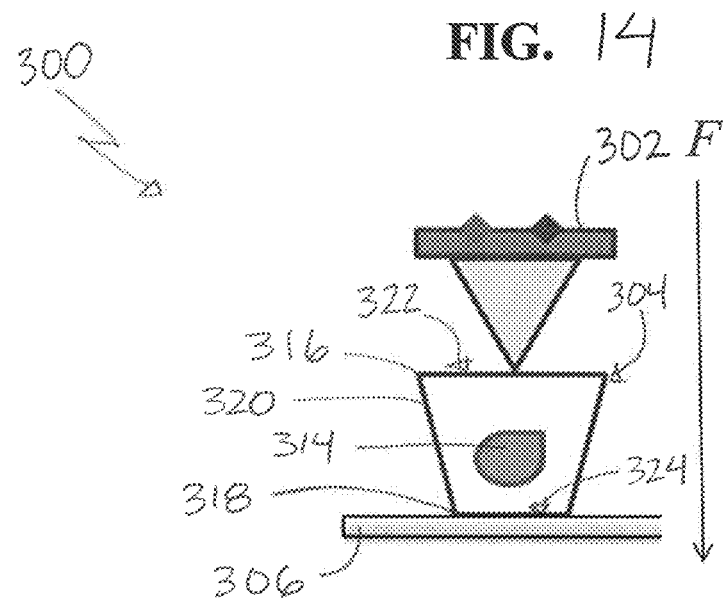
FIG. 15A is a plan view of the sample processing device showing a tissue sample inserted in the pulverization chamber in accordance with some embodiments of the invention.

FIG. 15A is a plan view of sample processing device 300 showing tissue sample 314 inserted in pulverization chamber 304 in accordance with some embodiments of the invention. As depicted, in some embodiments, the tissue sample 314 can be any type or mixture of plant tissue, including, but not limited to, seed, leaf, husk or bark, or any other single type of plant tissue(s) or mixture of plant tissue types. In some embodiments of the invention, the pulverization chamber 304 can include an upstream end 316, a downstream end 318, a side wall 320, an upstream opening 322, and a downstream opening 324. In some embodiments, the pulverization chamber 304 can be defined by an upstream end 316 and a downstream end 318, which are joined by side wall 320. In some embodiments of the invention, the upstream end 316 can define an upstream opening 322, which has a generally circular shape and is sized to permit tissue sample 314 to be inserted into the pulverization chamber 304, where pulverization of tissue sample 314 can help to break down the components of tissue sample 314, such as cell walls, in order to access nucleic acids. As shown, in some embodiments, the pulverization chamber 304 can include an overall frustoconical shape, which tapers towards the first separation element 306. In some embodiments, the frustoconical shape of pulverization chamber 304 can help drive materials towards the extraction chamber 308 (not shown in FIG. 15A). In some embodiments, the downstream end 318 can define a downstream opening 324, which in some embodiments, can permit a flow of materials from pulverization chamber 304 to enter the extraction chamber 308.

Figure 15B:
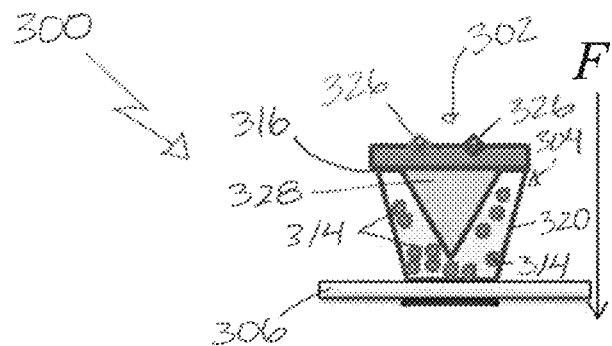
FIG. 15B is a plan view of the sample processing device showing the pulverization chamber with a cap coupled and shows the tissue sample in a pulverized state in accordance with some embodiments of the invention.

FIG. 15B is a plan view of the sample processing device 300 showing pulverization chamber 304 with cap 302 coupled and showing the tissue sample 314 in a pulverized state in accordance with some embodiments of the invention. As shown in FIG. 15B, in some embodiments, the cap 302 can cover an upstream opening 322. In some embodiments, the cap 302 can include ports 326, and grinder 328. In some embodiments, the cap 302 can be a snap-fit or twist-fit on to the upstream end 316.

In operation, a tissue sample 314 can be loaded into the pulverization chamber 304 and pulverized (e.g., the tissue sample 314 can be broken in smaller pieces.) The tissue sample 314 can be pulverized in different ways. For example, in some embodiments, the side wall 320 of pulverization chamber 304 can be formed from a flexible material that can be compressed by mechanical means (e.g., such as a handheld or machine operated pliers or other constriction.) As the pulverization chamber 304 is compressed, the tissue sample 314 can be crushed into smaller pieces. In some embodiments, to aid in the pulverization process, the interior of the pulverization chamber 304 can be configured to include an abrasive or corrugated surface, which can help to break down tissue sample 314. In some other embodiments, conventional pliers, or other mechanical means can also be inserted into the pulverization chamber 304 to directly pulverize the tissue sample 314. Additionally, in some further embodiments, an abrasive corrugated surface can be inserted into chamber 304, and a friction between the abrasive surface and the grinder 328 of cap 302 can be used to break tissue sample 314 into smaller pieces. In some embodiments, the grinder 328 can then be spun to break down tissue sample 314. In some embodiments, the tissue sample 314 can be dehydrated or flash frozen prior to being inserted into pulverization chamber 304 to make the tissue sample 314 more brittle and easier to pulverize.

Figure 16:
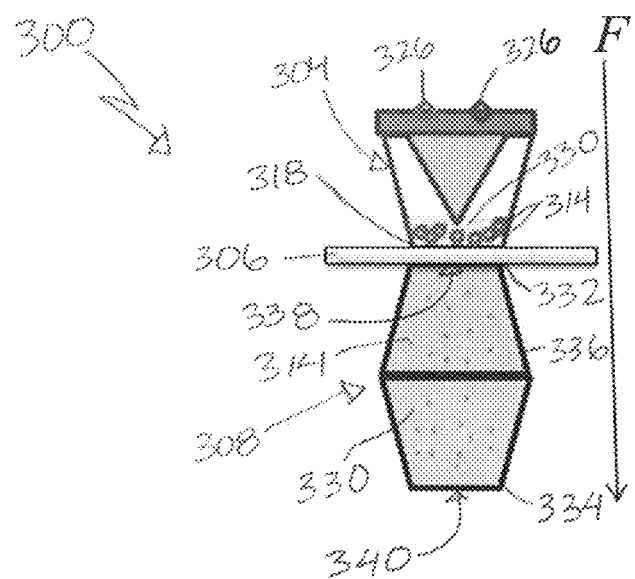
FIG. 16 is a plan view of the sample processing device showing an extraction chamber with the tissue sample and an extraction buffer disposed therein in accordance with some embodiments of the invention.

FIG. 16 is a plan view of sample processing device 300 showing extraction chamber 308 with tissue sample 314 and extraction buffer 330 disposed therein in accordance with some embodiments of the invention. In some embodiments, the extraction chamber 308 can include an upstream end 332, a downstream end 334, a side wall 336, an upstream opening 338, and a downstream opening 340, and a first separation element 306. In some embodiments, the extraction chamber 308 can be defined by the upstream end 332 and the downstream end 334, which are joined by side wall 336. In some embodiments of the invention, the upstream end 332 can comprise a frustoconical shape which tapers away from the downstream end 334. In some embodiments, the upstream end 332 can define an upstream opening 338, which permits flow from the pulverization chamber 304 to enter extraction chamber 308. In some embodiments of the invention, the frustoconical shape of the upstream end 332 can help to disperse components within extraction chamber 308 upon entry. In some embodiments, the downstream end 334 can include a frustoconical shape which tapers away from upstream end 332. In some embodiments of the invention, the downstream end 334 defines a downstream opening 340, which permits flow from extraction chamber 308 to enter dilution chamber 312 (not shown). In some embodiments, the frustoconical shape of downstream end 334 can help drive components towards dilution chamber 312.

In operation, the tissue sample 314 can be pulverized as described above with respect to FIGS. 15A and 15B. In some embodiments, once the tissue sample 314 is pulverized, an extraction buffer 330 can be supplied to the pulverization chamber 330 through one of ports 326, and the other port 326 can act as a pressure relief vent. In some embodiments of the invention, the extraction buffer 330 can be any one of many conventional buffers or mixtures of conventional buffers, including, but not limited to, Sodium Hydroxide (NaOH) based buffers. As an example embodiment, a suitable buffer can be formed from NaOH and Sodium Dodecyl (luryl) Sulfate (SDS). SDS is a surfactant that can help to solubilize a cell membrane, while NaOH can help to break down the cell wall and disrupts hydrogen bonding between DNA bases (and thus converting the double-stranded DNA into single-stranded DNA.)

In some embodiments of the invention, after a sufficient amount of extraction buffer 330 is added to pulverization chamber 304, air can be supplied through both of ports 326, shown in order to force material though the first separation element 306 and into extraction chamber 308. In other embodiments, a vacuum line can be coupled to one of ports 350 shown in FIG. 17A to pull material through first separation element 306 instead of using air pressure supplied through ports 326. In some further embodiments, air pressure can be supplied through ports 326 while a vacuum is applied through ports 350. In another embodiment, centrifuge action can be used to push material through the first separation element 306 instead of air pressure or vacuum.

As shown in FIG. 16, in some embodiments of the invention, the first separation element 306 can be disposed between the downstream end 318 of the pulverization chamber 304 and the upstream end 332 of extraction chamber 308. In some embodiments, the first separation element 306 can be configured to filter the flow of materials between the pulverization chamber 304 and extraction chamber 308. As a non-limiting example embodiment, the first separation element 306 can be a conventional filter or a screen. In some embodiments, the filter or screen can be designed to block some of the larger pulverized tissue samples 314 but can allow individual cells, organelles, etc. to pass through first separation element 306. In other embodiments, first separation element 306 can be a bursting membrane configured to burst when the pressure inside pulverization chamber 304 (generated by air passed through ports 326) exceeds a threshold value. When the membrane bursts, all the contents of pulverization chamber 304 can be free to enter extraction chamber 308.

In some embodiments, a portion of the pulverized tissue sample 314 and extraction buffer 330 can enter the extraction chamber 308 after passing through the first separation element 306. In some embodiments, the extraction buffer 330 can function as stated above to extract nucleic acids such as DNA and/or other components from the pulverized tissue sample 314. In some embodiments of the invention, in order to aid the extraction process, the tissue 314 and extraction buffer 330 in extraction chamber 308 can be heated. The exact temperature to which the tissue 314 and extraction buffer 330 in extraction chamber 308 is heated can depend on which extraction buffer 330 is used. Typically, tissue 314 and extraction buffer 330 in extraction chamber 308 can be heated to anywhere from about 65 degrees Celsius (about 149 degrees Fahrenheit) to about 80 degrees Celsius (about 176 degrees Fahrenheit). In some embodiments, heating can be applied either locally to the extraction chamber 308, or generally to the entire device 300. In some embodiments, following the heating, the tissue 314 and the extraction buffer 330 in extraction chamber 308 can be cooled to room temperature. In some embodiments, after the heating and cooling, the extraction chamber 308 can include some pulverized tissue sample 314 and extracted nucleic acids 352.

Figure 17A:
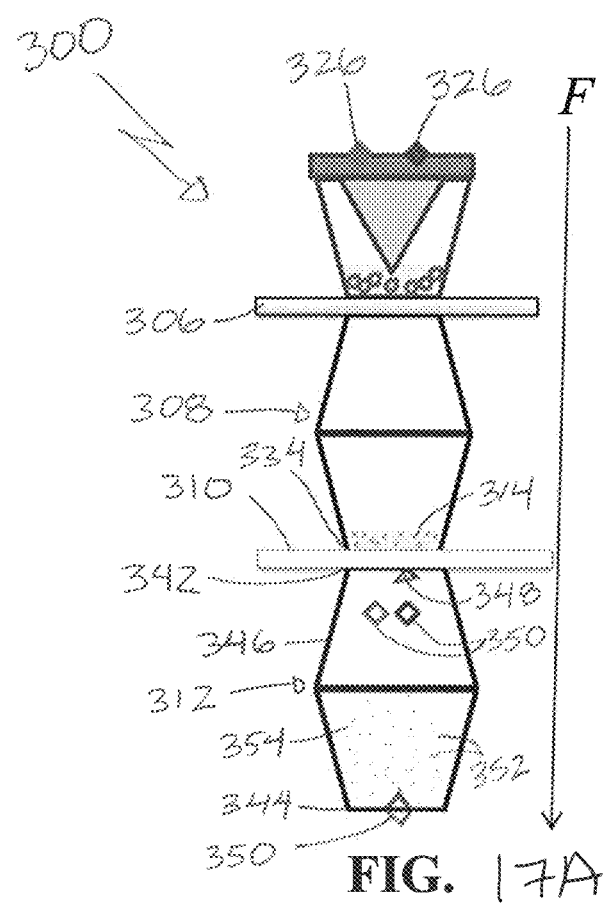
FIG. 17A is a plan view of the sample processing device showing a dilution chamber in accordance with some embodiments of the invention.

FIG. 17A is a plan view of sample processing device 300 showing dilution chamber 312. In some embodiments, the dilution chamber 312 can include an upstream end 342, downstream end 344, side wall 346, upstream opening 348, and ports 350. FIG. 17A also shows second separation element 310, and extracted nucleic acids 352 and neutralization buffer 354. In some embodiments, the dilution chamber 312 can be defined by the upstream end 342 and downstream end 344, which are joined by side wall 346. In some embodiments, the upstream end 342 can include a frustoconical shape which tapers away from downstream end 344. In some embodiments, the upstream end 342 defines upstream opening 348, which permits flow from extraction chamber 308 to enter dilution chamber 312. In some embodiments, the frustoconical shape of upstream end 342 can help to disperse components within dilution chamber 312 upon entry. In some other embodiments of the invention, the downstream end 344 has a frustoconical shape which tapers away from upstream end 342. In some embodiments, the dilution chamber 312 can include ports 350. As illustrated, in some embodiments, the two of ports 350 can be located proximate to upstream end 342, and one of ports 350 can be located proximate to the downstream end 344. In some embodiments, the frustoconical shape of downstream end 344 can help drive components towards port 350.

FIG. 17A shows extracted nucleic acid 352 in dilution chamber 312 and pulverized tissue 314 in extraction chamber 308. In order to separate extracted nucleic acid 352 and pulverized tissue 314, in some embodiments, air can be forced through ports 326 causing extracted nucleic acid 352 to pass through the second separation element 310. In some embodiments, the second separation element 310 can be disposed between the downstream end 334 of extraction chamber 308 and the upstream end 342 of dilution chamber 312. In some embodiments, the second separation element 310 can be a filter or screen that is configured to filter smaller particles than first separation element 306. Specifically, in some embodiments, the second separation element 310 can be sized to not allow pulverized tissue sample 314 to pass through. Thus, in some embodiments, extracted nucleic acid 352 and pulverized tissue sample 314 can be separated using the process as described.

In other embodiments of the invention, a vacuum line can be coupled to one of ports 350 to pull extracted nucleic acid 352 through second separation element 310 instead of using air pressure supplied through ports 326. In some further embodiments, air pressure can be supplied through ports 326 while a vacuum is applied through ports 350. In another embodiment of the invention, a centrifuge action can be used to push extracted nucleic acid 352 through second separation element 310 instead of air pressure or vacuum.

In some embodiments of the invention, after isolated nucleic acid 352 is supplied to dilution chamber 312, neutralizing buffer 354 can be supplied through one of the ports 350. In some embodiments, the neutralizing buffer 354 can serve to bring the pH of the solution in dilution chamber 312 to a suitable level for storing isolated nucleic acid 352. There are many suitable neutralizing buffers that can be used with embodiments of the invention, including, but not limited to Tris-Hydrochloride (TRIS-HCl).

Figure 17B:
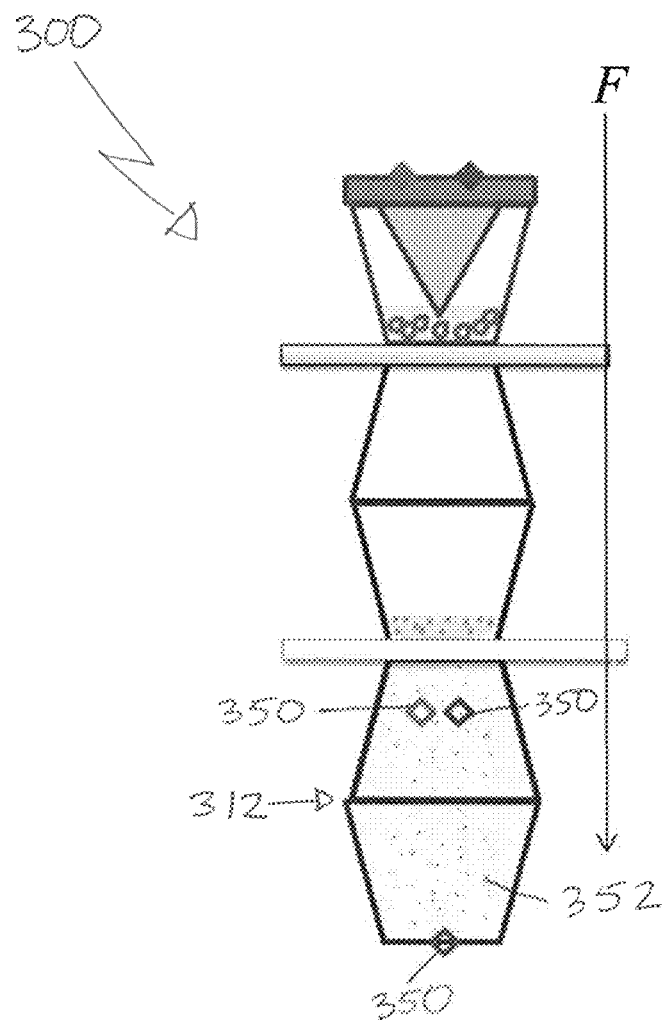
FIG. 17B is a plan view of the sample processing device showing a diluted isolated nucleic acid sample in accordance with some embodiments of the invention.

FIG. 17B is a plan view of sample processing device 300 showing diluted isolated nucleic acid sample 352. In some embodiments, the solution can be diluted using water or a buffer. There are many suitable buffers for dilution of nucleic acids. An example of a suitable dilution buffer is Tris-EDTA (TE) buffer. In some embodiments, after the isolated nucleic acid 352 is diluted, the dilution chamber 312 can be removed from sample processing device 300 directly, and isolated nucleic acid 352 can be stored therein. In some embodiments, the isolated nucleic acid 352 can also be dispensed into a vial through port 350. Once in the vial, isolated nucleic acid 352 can be amplified using polymerase chain reaction (PCR) and analyzed using fluorescence scanning techniques. In some embodiments, isolated nucleic acid 352 can also be aspirated through port 350 directly to a sample vial or an inline amplification device that can amplify the nucleic acids and analyze them using fluorescence scanning techniques.

Figure 18:
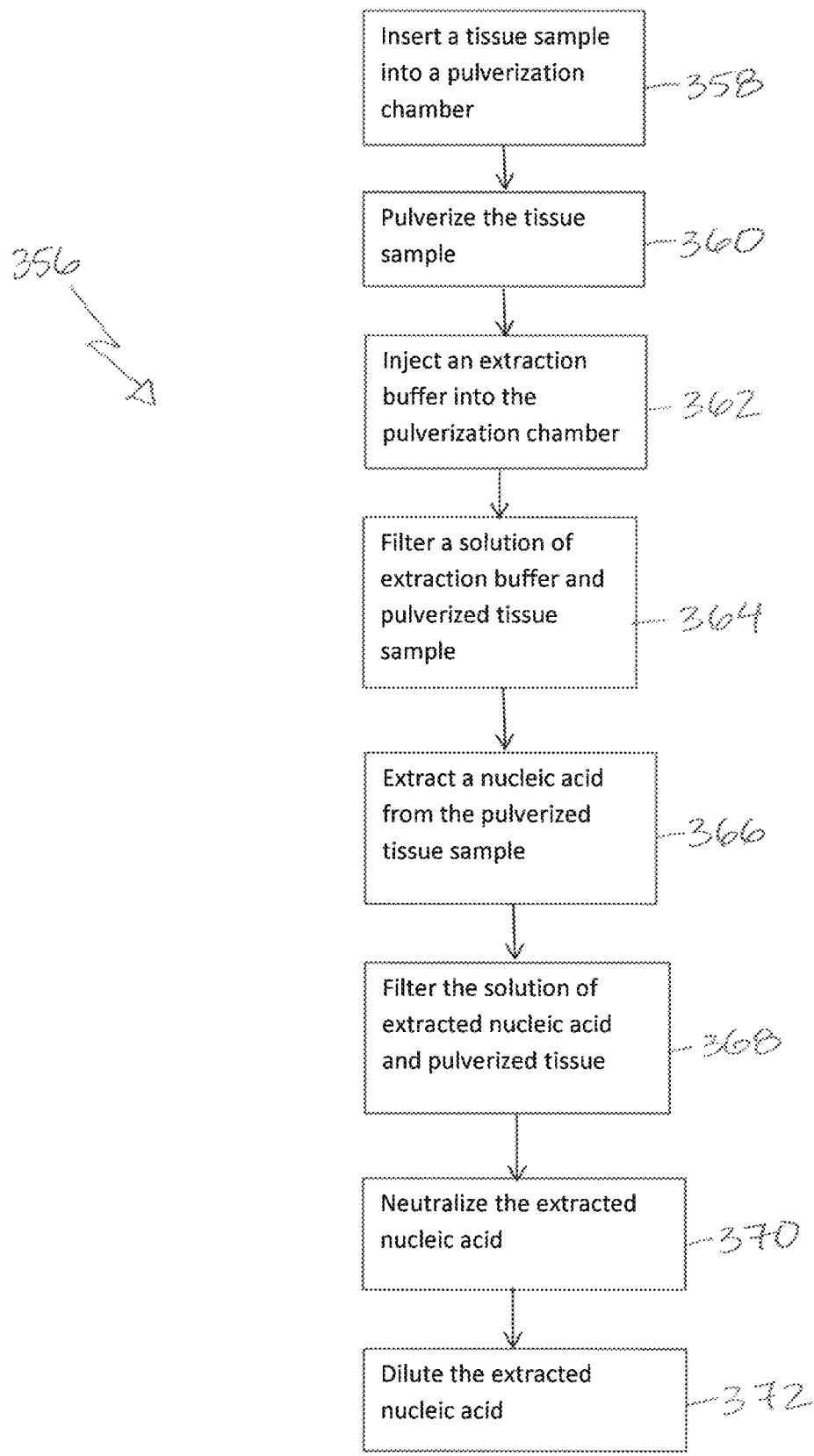
FIG. 18 is a flow diagram showing a method for performing an inline extraction of a nucleic acid from a tissue sample in accordance with some embodiments of the invention.

FIG. 18 is a flow diagram showing a method 356 for performing an inline extraction and amplification of a nucleic acid in accordance with some embodiments of the invention. In some embodiments, the method 356 can include an insertion step 358, and/or a pulverization step 360, and/or an injection step 362, and/or a filtration step 364, an/or an extraction step 366, an/or a filtration step 368, and/or a neutralization step 370, and/or a dilution step 372. In other embodiments, any of the steps 358, 360, 362, 364, 366, 368, 370, 372 can proceed in a different order than shown. Further, in some embodiments, any of the steps 358, 360, 362, 364, 366, 368, 370, 372 can be included, omitted, or repeated. In some embodiments of the invention, during an insertion step 358, a tissue sample 314 can be loaded into the pulverization chamber 304 of the multi-module inline sample processing device 300. In some embodiments of the invention, during a pulverization step 360, the tissue sample 314 can be pulverized into a powder. Further, in some embodiments, following the step 360, during an injection step 362, an extraction buffer 330 can be added to the pulverization chamber 304. In some embodiments, the filtration step 364 can follow the injection step 362. In some embodiments, during the filtration step 364, the solution of extraction buffer 330 and the pulverized tissue sample 314 can be forced through the first separation element 306 and into extraction chamber 308 of sample processing device 300. In some embodiments of the invention, following the filtration step, during the extraction step 366, the solution of extraction buffer 330 and the pulverized tissue sample 314 can be heated and then cooled to room temperature. In some embodiments, the filtration step 368 follows the extraction step 366. In some embodiments, during the filtration step 368, extracted nucleic acid 352 can be filtered through the second separation element 310 and into the dilution chamber 312. In some embodiments of the invention, the pulverized tissue sample 314 can remain in the extraction chamber 308. In some embodiments, following the filtration step 368, during the neutralization step 370, a neutralization buffer 354 can be added to dilution chamber 312 to neutralize isolated nucleic acid 352. In some embodiments, following the neutralization step 370, during a dilution step 372, water or a dilution buffer can be added to the dilution chamber 312. In some embodiments, following these steps as described above, isolated nucleic acid 352 can be stored, and/or aspirated to an inline device to perform nucleic acid amplification, and/or or dispensed into a sample vial that can be inserted into an amplification device.

Figure 19:
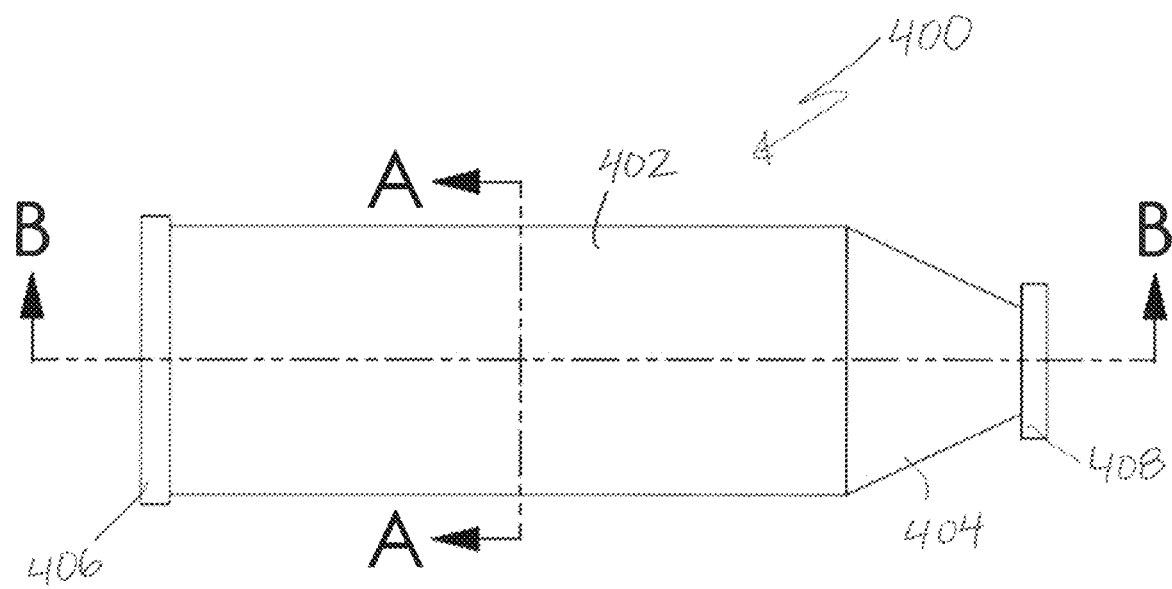
FIG. 19 is side view of a sample processing device for pulverizing and denaturing in accordance with some embodiments of the invention.
Figure 20:
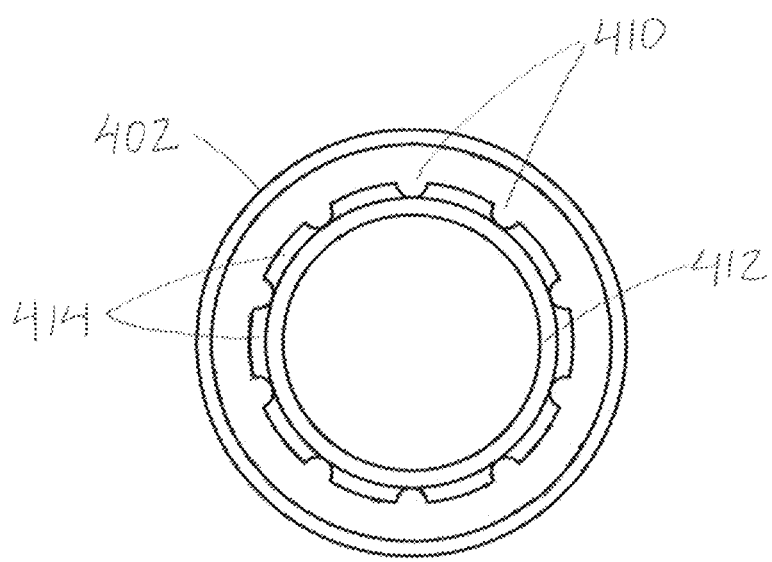
FIG. 20 is a cross-sectional view of the sample processing device of FIG. 19 along line A-A.
Figure 21A:
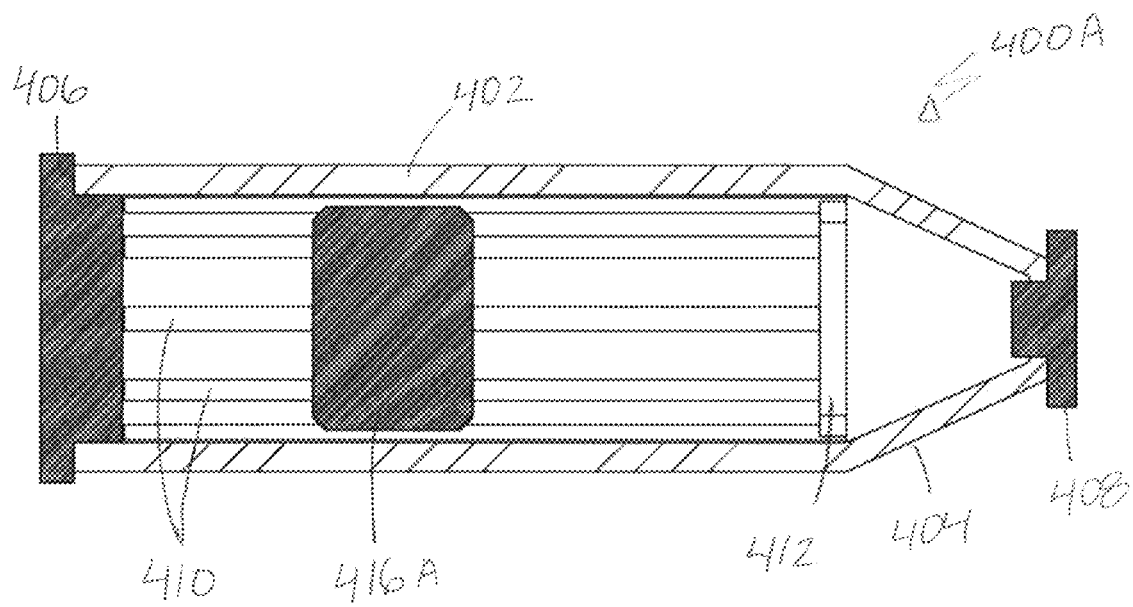
FIG. 21A is a cross-sectional view of one embodiment of the sample processing device of FIG. 19.
Figure 21B:
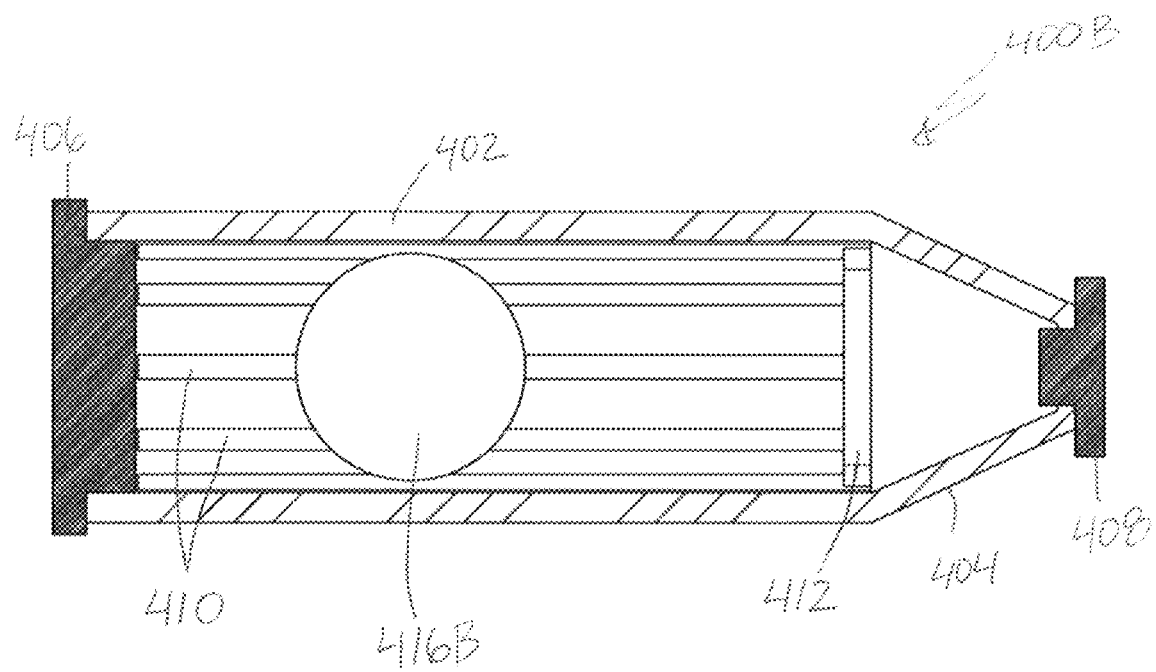
FIG. 21B is a cross-sectional view of another embodiment of the sample processing device of FIG. 19.

FIG. 19 is a side view of sample processing device 400 in accordance with some embodiments of the invention, and FIG. 20 is a cross-sectional view of the sample processing device 400 along line A-A in FIG. 19. FIG. 21A is a cross-sectional view of sample processing device 400A, one embodiment of sample processing device 400 shown in FIGS. 1 and 2. FIG. 21B is a cross-sectional view of sample processing device 400B, another embodiment of sample processing device 400 shown in FIGS. 1 and 2. In some embodiments of the invention, the sample processing devices 400, 400A, 400B are advantageous because they reduce the risk of contamination when pulverizing and denaturing a sample to prepare the sample for testing. Devices 400, 400A, 400B can eliminate the need to perform pulverization in one vessel and transfer the pulverized sample into another vessel for denaturing, thus reducing opportunities for contamination of the sample.

In some embodiments of the invention, the sample processing devices 400, 400A, and 400B can be disposable tubes. In some embodiments, the sample processing devices 400, 400A, and 400B can include a cylindrical portion 402 coupled or integrated with a tapered portion 404, cap 406, cap 408, ribs 410, and ring 412. In some embodiments of the invention, the cylindrical portion 402 and tapered portion 404 can be at least partially hollow. In some embodiments, the cap 406 can at least partially cover the end of cylindrical portion 402, and the cap 408 can at least partially cover the end of tapered portion 404. In some embodiments, the ribs 410 and ring 412 can be coupled to the cylindrical portion 402 of the sample processing device 400. Further, in some embodiments, the ribs 410 can extend along cylindrical portion 402. Some embodiments include a ring 412 that is located at the end of ribs 410 proximate or adjacent to where the cylindrical portion 402 meets the tapered portion 404.

In some embodiments of the invention, the sample processing devices 400A and 400B can be similar to sample processing device 400, except sample processing device 400A can include a pulverizer 400A, and sample processing device 400B can include a pulverizer 400B. As shown in FIG. 21A, in some embodiments, the pulverizer 416A can be cylindrically shaped. As shown in FIG. 21B, in some embodiments, the pulverizer 416B can be spherically shaped. The following description references sample processing device 400A as shown in FIG. 21A, but the description can apply to both sample processing device 400A and sample processing device 400B.

In some embodiments of the invention, the pulverizer 416A can be contained within cylindrical portion 402. In some embodiments, the ring 412 can prevent the pulverizer 416A from sliding into the tapered portion 404 of the sample processing device 400A. In alternative embodiments of the invention, the pulverizer 416A can be any shape that can be contained by ribs 410 and ring 412 within cylindrical portion 402 of sample processing device 400A. In some embodiments, the ribs 412 can prevent the pulverizer 416A from touching the sides of sample processing device 400, and can allow the pulverizer 416A to slide within cylindrical portion 402. In some embodiments, the pulverizer 416A can be any non-reactive material such as glass, ceramic, stainless steel, or any non-reactive polymer.

In some embodiments of the invention, the sample processing device 400A can enable a crude sample to be both pulverized and denatured in the same vessel. In some embodiments, in order to pulverize and denature a sample, the cap 406 can be removed from the end of cylindrical portion 402, and pulverizer 416A can be placed within the cylindrical portion 402. In some embodiments of the invention, the crude sample can be placed into the cylindrical portion 402. The crude sample can be one or more pieces of corn, one or more seed or seed portions, one or more leaves or leave portions, combinations thereof, or any other solid biological sample. In some embodiments of the invention, once the crude sample and pulverizer 416A are placed within cylindrical portion 402, the cap 406 can be placed back on the end of cylindrical portion 402. In an alternative embodiment of the invention, the sample processing device 400A can be manufactured with pulverizer 416A already contained within cylindrical portion 402, and the crude sample can be added into either the cylindrical portion 402 through the cap 406 or the tapered portion 404 through the cap 408.

In some embodiments of the invention, once the crude sample and pulverizer 416A are at least partially sealed within sample processing device 400A, the sample processing device 400A can be placed into an instrument, such as a shaker, with the cap 406 facing down. In some embodiments, the instrument can shake the sample processing device 400A such that the pulverizer 416A can move against the ribs 410 and slide within cylindrical portion 402 to macerate the crude sample. In some embodiments, once the sample has been pulverized, the sample processing device 400A can be removed from the instrument. In some embodiments, the cap 408 can then be removed from the tapered portion 404, and a denaturing agent, such as sodium hydroxide, can be added into the tapered portion 404. In some embodiments, the tapered shape of the tapered portion 404 and ring 412 can prevent the pulverizer 416A from sliding into the tapered portion 404 when the denaturing agent is added. In some embodiments, this can reduce the risk of contamination by ensuring that pulverizer 416A is contained within cylindrical portion 402, and is prevented from sliding out of the sample processing device 400A. In some embodiments, after the denaturing agent has been added, the cap 408 can be placed back on the tapered portion 404.

In some embodiments, once the denaturing agent and pulverized sample are at least partially sealed within the sample processing device 400A, the sample processing device 400A can be placed back into the instrument with the cap 408 facing down. In some embodiments, the instrument can shake the sample processing device 400A such that the denaturing agent at least partially denatures the DNA within at least a portion of the pulverized sample. In some embodiments, the gaps between the ribs 410 can allow the denaturing agent to flow within the cylindrical portion 402 in addition to the tapered portion 404 in order to denature the entire pulverized sample. In some embodiments, once at least a portion of the DNA within at least a portion of the sample has been denatured, at least a portion of the denatured sample can be transferred into a separate vessel for testing, or the portion of the denatured sample can be tested in sample processing device 400A. In some embodiments, if the denatured sample is transferred to a separate vessel, the cap 408 can be opened in order to transfer the sample. In some embodiments of the invention, the tapered portion 404 and ring 412 can prevent the pulverizer 416A or pulverizer 416B from sliding out of sample processing device 400A when the denatured sample is being transferred.

Figure 22:
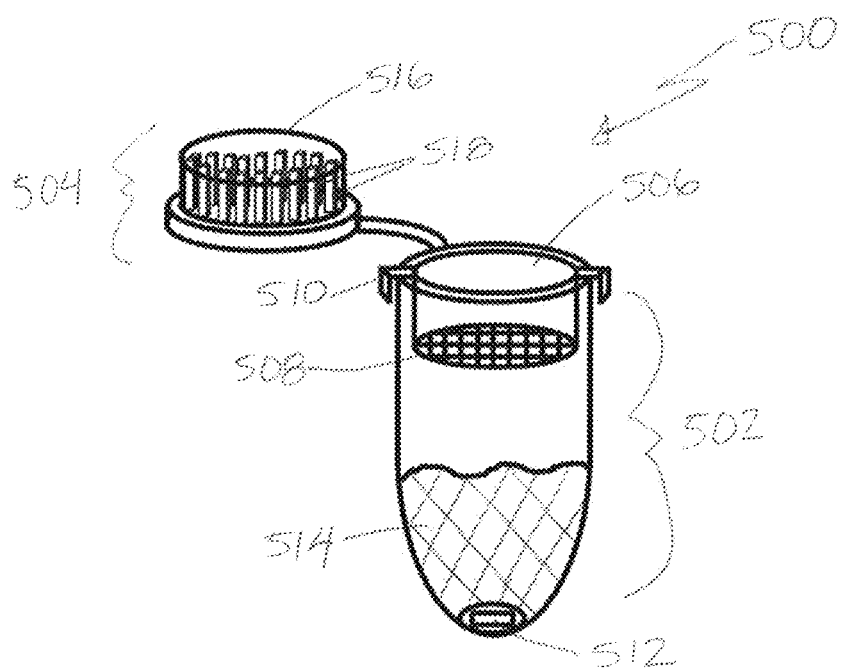
FIG. 22 is a perspective view of a sample processing device in accordance with some embodiments of the invention.

FIG. 22 is a perspective view of sample processing device 500 in accordance with some embodiments of the invention. In some embodiments, the sample processing device 500 can include tube 502 and cap 504. In some embodiments of the invention, the tube 502 can include basket 506 with grid 508 and tabs 510. In some embodiments, the tube 502 can also include a barcode 512, and can be filled with lysis buffer 514 that can lyse cells within a macerated sample prepared within the device 500 in order to expose the DNA within the cells for further testing.

In some embodiments, the basket 506 can be a removable basket that sits in tube 502 with tabs 510 hanging over the edge of the tube 502. In some embodiments, the cap 504 can include a punch edge 516 and fingers 518. In some embodiments, the sample processing device 500 can be used to take a sample of a crude biological material, such as a leaf, seed, or clip from an ear of corn, and force the sample through the grid 508 of the basket 506 to macerate the sample. In some embodiments, the macerated sample can be combined with the lysis buffer 514 to extract at least some DNA from the sample for further testing.

In some embodiments, in order to take and process a sample with sample processing device 500, some crude biological material can be placed on top of tube 502, and the cap 504 can be coupled to the tube 502 to at least partially seal the tube 502. In some embodiments, the cap 504 can be a snap top cap. In some embodiments, as the cap 504 is snapped into place, the punch edge 516 can punch a sample out of the crude biological sample and into the basket 506. In some embodiments, the punch edge 516 can be a ring-shaped sharp edge suitable for cutting a crude biological sample. In some embodiments, as the cap 504 is snapped into place, the fingers 518 can force the sample through the grid 508 of basket 506 to macerate the sample. In some embodiments, the macerated sample can then fall into lysis buffer 514. In some embodiments, the grid 508 and fingers 518 can be made of a polymer, a metal (e.g., such as aluminum or stainless steel), a composite material, a ceramic or glass, or combinations thereof.

In some embodiments of the invention, the closing cap 504 can cause the tabs 510 to break off of basket 506 such that basket 506 with any macerated sample remaining on the grid 508 can fall into the lysis buffer 514. In an alternative embodiment of the invention, the closing cap 504 can cause the tabs 510 to break off the basket 506 so that the cap 504 can be completely sealed on the tube 502, but the basket 506 does not fall into the lysis buffer 514. In some embodiments of the invention, this can enable the macerated sample to be kept separate from lysis buffer 514 before combining the macerated sample and lysis buffer 514. In some embodiments, the tabs 510 can ensure that the sample processing device 500 can be used only once, thus avoiding potential combining of biological samples when collecting multiple samples into multiple sample processing devices. In an alternative embodiment, sample processing device 500 can be used without lysis buffer 514. In this alternative embodiment, sample processing device 500 can be used to punch and macerate a sample and store the macerated sample for future testing.

Figure 23:
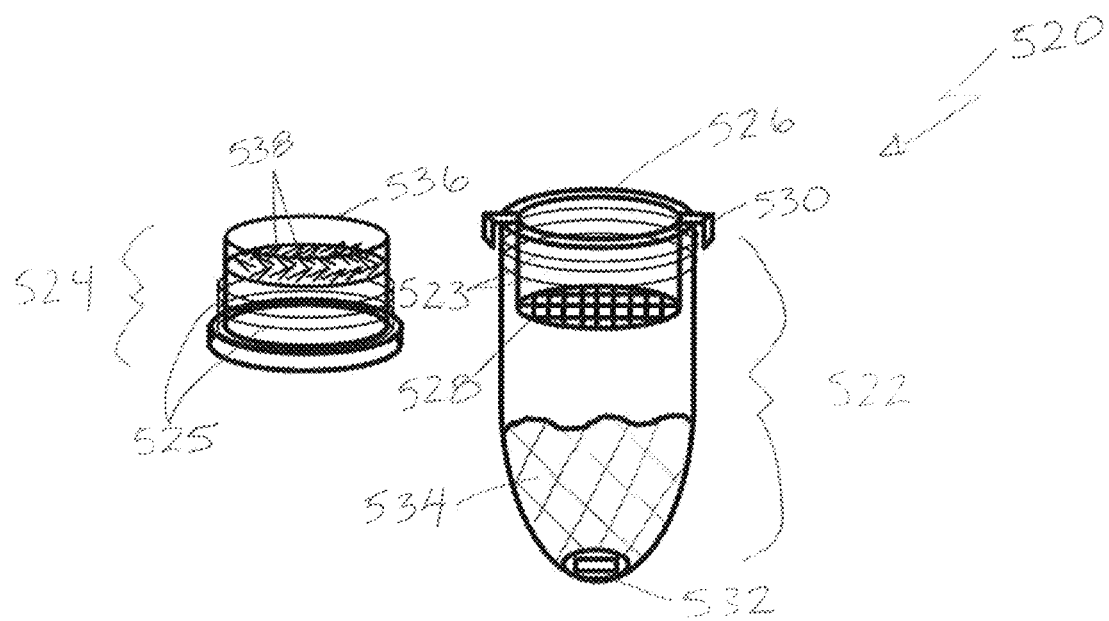
FIG. 23 is a perspective view of another embodiment of the sample processing device of FIG. 22.

FIG. 23 is a perspective view of sample processing device 520, another embodiment of sample processing device 500 in FIG. 22. In some embodiments, the sample processing device 520 can include a tube 522 with internal threads 523 and cap 524 with external threads 525. In some embodiments, the cap 524 can include punch edge 536 and teeth 538. In some embodiments, the tube 522 can include basket 526 with grid 528 and tabs 530. In some embodiments, the basket 526 can be a removable basket that sits in tube 522 with tabs 530 hanging over the edge of tube 522. In some embodiments, the tube 522 can also include barcode 532, and can be filled with lysis buffer 534.

In some embodiments of the invention, the sample processing device 520 can function in substantially the same manner as sample processing device 500 in FIG. 22, except cap 524 can include teeth 538 instead of fingers 518. Further, cap 524 can screw into the tube 522 instead of snapping onto tube 522; external threads 525 of cap 524 fit into internal threads 523 of tube 522. In some embodiments, in order to take and process a sample with sample processing device 520, crude biological material can be placed on top of tube 522. As cap 524 is threaded into tube 522, punch edge 536 can punch a sample out of the crude biological sample into basket 526. Further, in some embodiments, as cap 524 is threaded into tube 522, teeth 518 grind the sample against and/or through grid 528 of basket 526 to macerate the sample. In alternative embodiments, teeth 518 can be another textured surface that can grind at least a portion of the sample against and/or through grid 528 which can then fall into the lysis buffer 534. In some embodiments, closing cap 524 can cause the tabs 530 to break off of the basket 526 so that basket 526 with any macerated sample remaining on grid 528 falls into lysis buffer 534.

Figure 24:
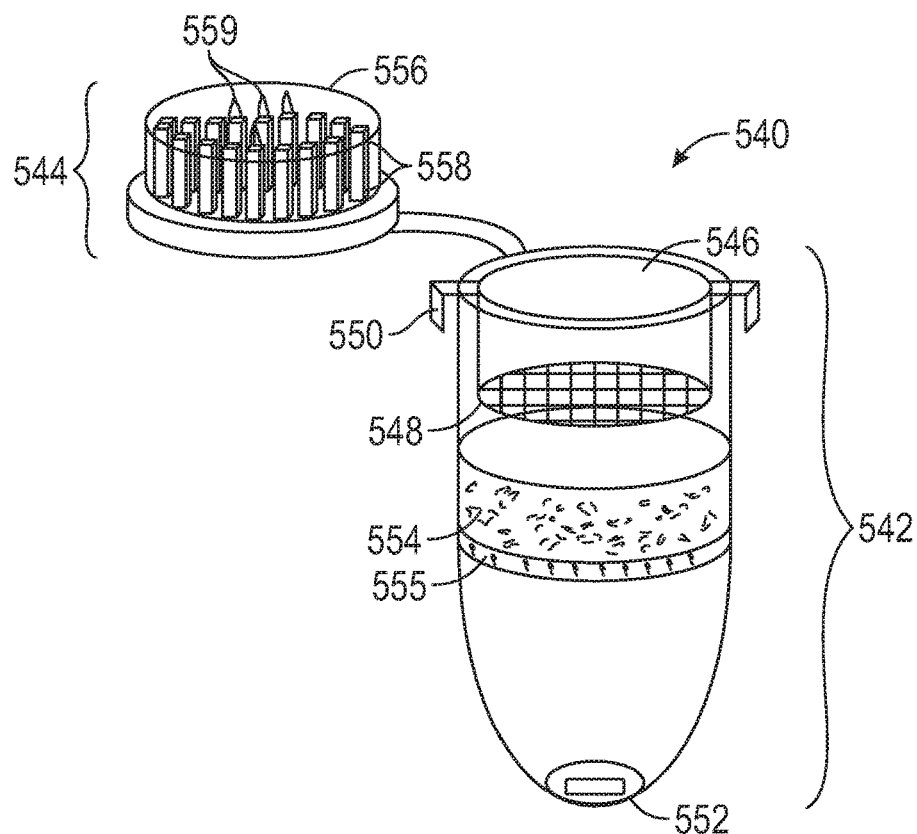
FIG. 24 is a perspective view of another embodiment of the sample processing device of FIG. 22.

FIG. 24 is a perspective view of sample processing device 540, another embodiment of sample processing device 500 in FIG. 22. In some embodiments, the sample processing device 540 can include tube 542 and cap 544. In some embodiments, the tube 542 includes basket 546 with grid 548 and tabs 550. In some embodiments, the basket 546 can be a removable basket that sits in tube 542 with tabs 550 hanging over the edge of tube 542. Further, in some embodiments, the tube 542 can also include barcode 552, sodium hydroxide pouch 554, and permeable layer 555. Further, in some embodiments, the cap 544 can include a punch edge 556 and fingers 558 with piercers 559.

In some embodiments of the invention, the sample processing device 540 can function in substantially the same manner as sample processing device 500 in FIG. 22, except tube 542 includes sodium hydroxide pouch 554 and permeable layer 555 instead of lysis buffer 514. Additionally, in some embodiments, fingers 558 include piercers 559. In some embodiments of the invention, in order to take and process a sample with sample processing device 540, crude biological material can be placed on top of tube 542. In some embodiments, the cap 544 can be used to at least partially seal the tube 542. In some embodiments, as the cap 544 is snapped into place, the punch edge 556 can punch a sample out of the crude biological sample into basket 546. In some embodiments, as the cap 544 is snapped into place, the fingers 558 force the sample through grid 548 of basket 546 to macerate the sample, and piercers 559 can puncture the sodium hydroxide pouch 554. In the embodiment shown, cap 544 includes four piercers on fingers 558. In alternative embodiments, cap 544 can include a single piercer 559 or multiple piercers 559. In some embodiments of the invention, the piercers 559 can be sharp tips capable of puncturing the sodium hydroxide pouch 554.

In some embodiments of the invention, once the sodium hydroxide pouch 554 is pierced, the sodium hydroxide and the macerated sample can pass through the permeable layer 555 into the bottom of tube 542. In some embodiments of the invention, the permeable layer 555 can be a metal or plastic screen. In some embodiments, closing cap 544 can cause the tabs 550 to break off of basket 546 with any macerated sample remaining on grid 548 falls onto permeable layer 555. In some embodiments, the permeable layer 555 can allow the sodium hydroxide and macerated sample to pass through into the bottom of tube 542, but can prevent the basket 546 from passing into the bottom of tube 542. In some embodiments, the sodium hydroxide can denatures DNA within the macerated sample in order to expose the DNA within the cells for further testing.

Figure 25:
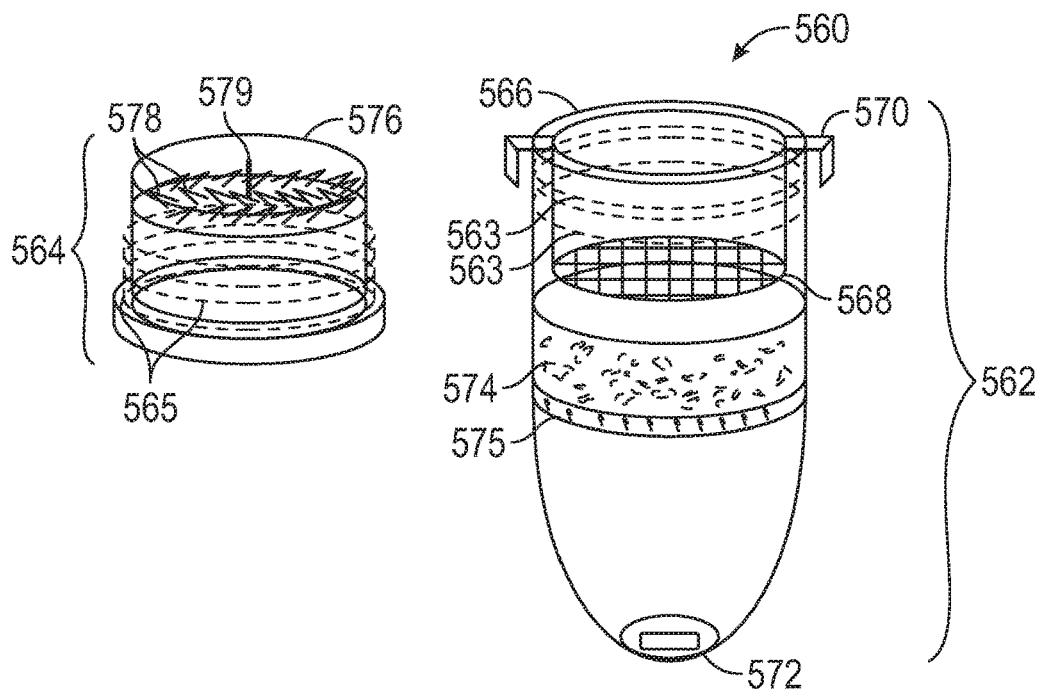
FIG. 25 is a perspective view of another embodiment of the sample processing device of FIG. 22.

FIG. 25 is a perspective view of sample processing device 560, another embodiment of sample processing device 500 in FIG. 22. In some embodiments, the sample processing device 560 can include tube 562 with internal threads 563 and cap 564 with external threads 565. In some embodiments, the tube 562 can include basket 566 with grid 568 and tabs 570. In some embodiments of the invention, the basket 566 can be a removable basket that sits in the tube 562 with tabs 570 hanging over the edge of tube 562. In some embodiments, the tube 562 also includes barcode 572, sodium hydroxide pouch 574, and permeable layer 575. Further, in some embodiments, the cap 564 can include punch edge 576, teeth 578, and piercer 579.

In some embodiments of the invention, the sample processing device 560 can function in substantially the same manner as sample processing device 540 in FIG. 24, except cap 564 includes teeth 578 instead of fingers 558. Additionally, in some embodiments, the cap 564 can screw into the tube 562 instead of snapping onto tube 562; external threads 565 of cap 564 fit into internal threads 563 of tube 562. In some embodiments of the invention, in order to take and process a sample with sample processing device 560, crude biological material can be placed on top of tube 562. In some embodiments, as cap 564 is threaded into the tube 562, the punch edge 576 can punch a sample out of the crude biological sample into basket 566. In some embodiments, as cap 564 is threaded into tube 562, the teeth 578 can grind the sample against and/or through grid 568 of basket 566 to macerate the sample, and piercer 579 can puncture the sodium hydroxide pouch 574. In some embodiments of the invention, the piercer 579 can be a needle-shaped projection.

In some embodiments of the invention, once the sodium hydroxide pouch 574 is pierced, sodium hydroxide and macerated sample can pass through permeable layer 575 into the bottom of tube 562. In some embodiments, closing the cap 564 can cause the tabs 570 to break off of basket 566 with any macerated sample remaining on the grid 568 falling onto the permeable layer 575. In some embodiments, the permeable layer 575 can allow the sodium hydroxide and macerated sample to pass through into the bottom of the tube 562 but can prevent the basket 566 from passing into the bottom of tube 562.

Figure 26:
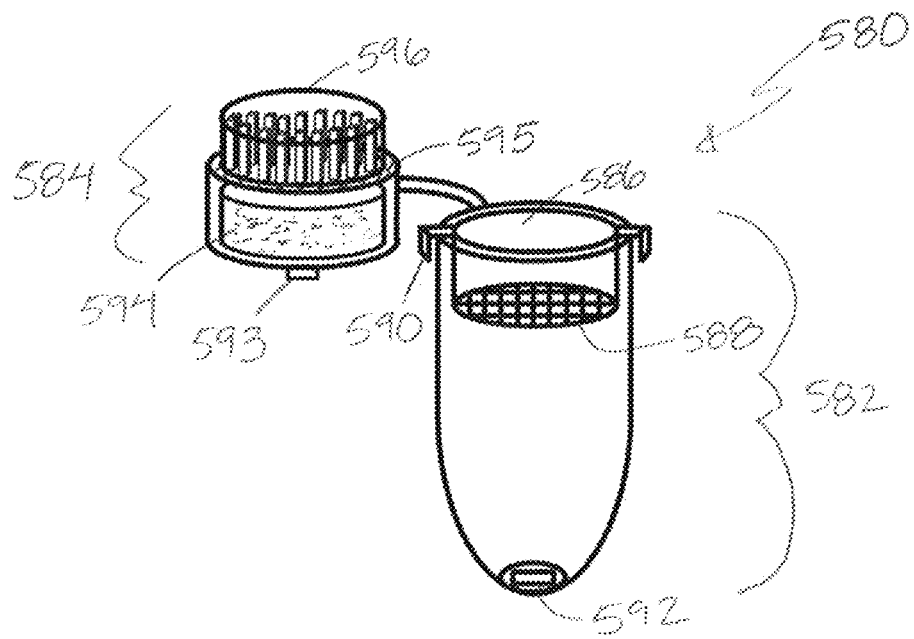
FIG. 26 is a perspective view of another embodiment of the sample processing device of FIG. 22.

FIG. 26 is a perspective view of sample processing device 580, another embodiment of sample processing device 500 in FIG. 22. Some embodiments include a sample processing device 580 that includes tube 582 and cap 584. In some embodiments, the tube 582 includes basket 586 with grid 588 and tabs 590. In some embodiments, the basket 586 can be a removable basket that sits in tube 582 with tabs 590 hanging over the edge of tube 582. In some embodiments, the tube 582 can also include barcode 592. In some embodiments, the cap 584 can include septum 593, sodium hydroxide pouch 594, permeable layer 595, punch edge 596, and fingers 558.

Some embodiments of the invention include a sample processing device 580 that functions in substantially the same manner as sample processing device 540 in FIG. 24, except cap 584 can include sodium hydroxide pouch 594 and septum 595, and the tube 582 does not include a sample processing liquid. In some embodiments, in order to take and process a sample with sample processing device 580, crude biological material can be placed on top of the tube 582, and the cap 584 can be used to seal the tube 582. In some embodiments, as cap 584 is snapped into place, the punch edge 596 can punch a sample out of the crude biological sample and into the basket 586. In some embodiments, as the cap 584 is snapped into place, the fingers 598 can force the sample through the grid 588 of basket 586 to macerate the sample. In some embodiments, closing the cap 584 can cause the tabs 590 to break off of the basket 586 so that the basket 586 with any macerated sample remaining on the grid 588 can fall into the bottom of tube 582.

In some embodiments, after cap 584 has been snapped into place, a piercing device, such as a needle, can be inserted into the septum 593 to pierce the sodium hydroxide pouch 594. In some embodiments of the invention, the septum 593 can be a resealable septum. In some embodiments, once the sodium hydroxide pouch 554 is pierced, sodium hydroxide passes through the permeable layer 595 and into the bottom of tube 582. In some embodiments, the permeable layer 595 can be a metal or plastic screen. In an alternative embodiment, the cap 584 can be made of a compressible material such that sodium hydroxide pouch 594 can be popped by applying pressure to cap 584.

Figure 27:
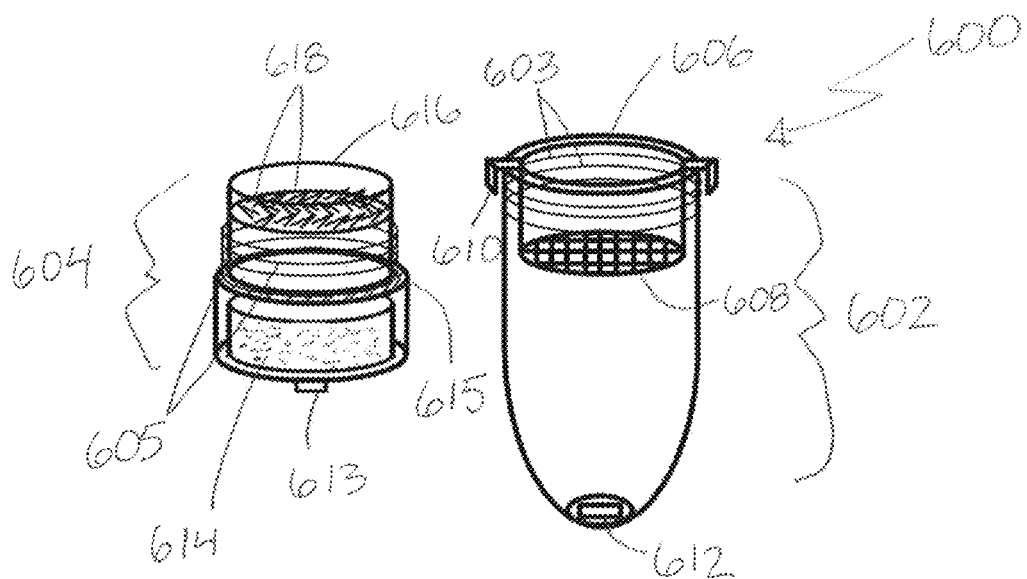
FIG. 27 is a perspective view of another embodiment of the sample processing device of FIG. 22.

FIG. 27 is a perspective view of sample processing device 600, another embodiment of sample processing device 500 in FIG. 22. In some embodiments, the sample processing device 600 can includes tube 602 with internal threads 603 and cap 604 with external threads 605. In some embodiments, the tube 602 can includes basket 606 with grid 608 and tabs 610. In some embodiments, the basket 606 can be a removable basket that sits in tube 602 with tabs 610 hanging over the edge of tube 602. In some embodiments, the tube 602 also includes barcode 612, and the cap 604 includes septum 613, sodium hydroxide pouch 614, permeable layer 615, punch edge 616, and teeth 618.

In some embodiments, the sample processing device 600 functions in substantially the same manner as sample processing device 580 in FIG. 26, except cap 604 includes teeth 618 instead of fingers 598. Additionally, in some embodiments, the cap 604 screws into the tube 602 instead of snapping onto the tube 602; external threads 605 of cap 604 fit into internal threads 603 of tube 602. In some embodiments, in order to take and process a sample with sample processing device 600, crude biological material is placed on top of tube 602. In some embodiments, as cap 604 is threaded into tube 602, punch edge 616 punches a sample out of the crude biological sample into basket 606. In some embodiments, as cap 604 is threaded into tube 602, teeth 618 can grind the sample against and/or through grid 618 of basket 606 to macerate the sample. In some embodiments, closing cap 604 causes tabs 610 to break off of basket 606 such that basket 606 with any macerated sample remaining on grid 608 falls into the bottom of tube 602.

In some embodiments, after cap 604 has been closed into place, a piercing device, such as a needle, can be inserted into septum 613 to pierce sodium hydroxide pouch 614. In some embodiments, once the sodium hydroxide pouch 614 is pierced, sodium hydroxide passes through permeable layer 615 into the bottom of tube 602. In an alternative embodiment, the cap 604 can be made of a compressible material where the sodium hydroxide pouch 614 can be popped by applying pressure to cap 604.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. Various features and advantages of the invention are set forth in the following claims.

The invention claimed is:

1. An inline sample processing device comprising:
   a first chamber configured to receive a tissue sample and a nucleic acid extraction reagent, the first chamber configured to permit the tissue sample to be pulverized therein;
   a second chamber in flow communication with the first chamber and configured to receive the extraction reagent and a portion of the pulverized tissue sample;
   a first separation element disposed between the first chamber and the second chamber and configured to permit a portion of the pulverized tissue sample and the extraction reagent to flow from the first chamber to the second chamber;
   a third chamber in flow communication with the second chamber, the third chamber having a plurality of ports configured to allow a reagent to be delivered to the third chamber; and
   a second separation element disposed between the second chamber and the third chamber and configured to substantially prevent the pulverized tissue from entering the third chamber.

2. A sample processing device for pulverization and denaturation, the sample processing device comprising:
   a hollow cylindrical portion;
   a hollow tapered portion;
   a first cap configured and arranged to cover an end of the cylindrical portion;
   a second cap configured and arranged to cover an end of the tapered portion;
   a plurality of ribs extending along the cylindrical portion;
   a ring at an end of the plurality of ribs where the cylindrical portion meets the tapered portion; and
   a pulverizer contained within the cylindrical portion between the ring and the first cap.

3. The sample processing device of claim 1, wherein the pulverizer is cylindrical or spherical.

4. The sample processing device of claim 2, wherein the pulverizer includes at least one of glass, ceramic, stainless steel, and a polymer.

5. The sample processing device of claim 2, wherein the plurality of ribs is configured and arranged to prevent the pulverizer from touching sides of the sample processing device and allows the pulverizer to slide within the cylindrical portion.

6. The sample processing device of claim 2, wherein the ring is configured and arranged to prevent the pulverizer from entering the tapered portion of the sample processing device.

7. A method for pulverizing and denaturing a crude sample, the method comprising:
   placing a pulverizer in a sample processing device, the sample processing device comprising:
   a cylindrical portion;
   a tapered portion;
   a plurality of ribs extending along the cylindrical portion; and
   a ring at an end of the plurality of ribs where the cylindrical portion meets the tapered portion;
   placing the crude sample in the cylindrical portion of the sample processing device;
   sealing the sample processing device;
   shaking the sample processing device such that the pulverizer macerates the crude sample to create a pulverized sample;
   adding a denaturing agent into the tapered portion of the sample processing device;
   sealing the sample processing device; and
   shaking the sample processing device such that the denaturing agent denatures DNA within the pulverized sample to create a denatured sample.

8. The method of claim 7, and further comprising transferring the denatured sample into a testing vessel.

9. The method of claim 7, and further comprising testing the denatured sample in the sample processing device.

* * * * *